US011407835B2

(12) United States Patent
Yates et al.

(10) Patent No.: US 11,407,835 B2
(45) Date of Patent: Aug. 9, 2022

(54) PHARMACEUTICAL COMPOSITION

(71) Applicant: UCB BIOPHARMA SRL, Brussels (BE)

(72) Inventors: Andrew Jeffrey Yates, Berkshire (GB); Jan Ivo Massant, Berkshire (GB)

(73) Assignee: UCB BIOPHARMA SRL, Brussels (BE)

(*) Notice: Subject to any disclaimer, the term of this patent is extended or adjusted under 35 U.S.C. 154(b) by 54 days.

(21) Appl. No.: 16/300,522

(22) PCT Filed: May 11, 2017

(86) PCT No.: PCT/EP2017/061261
§ 371 (c)(1),
(2) Date: Nov. 9, 2018

(87) PCT Pub. No.: WO2017/194646
PCT Pub. Date: Nov. 16, 2017

(65) Prior Publication Data
US 2020/0048346 A1 Feb. 13, 2020

(30) Foreign Application Priority Data
May 12, 2016 (GB) ..................... 1608323

(51) Int. Cl.
| A61K 39/395 | (2006.01) |
| C07K 16/28 | (2006.01) |
| A61K 9/19 | (2006.01) |
| A61K 47/18 | (2017.01) |
| A61K 47/22 | (2006.01) |
| A61K 47/26 | (2006.01) |

(52) U.S. Cl.
CPC .............. *C07K 16/283* (2013.01); *A61K 9/19* (2013.01); *A61K 47/183* (2013.01); *A61K 47/22* (2013.01); *A61K 47/26* (2013.01); *C07K 2317/21* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| 8,613,919 B1 | 12/2013 | Ma et al. |
| 10,233,243 B2 * | 3/2019 | Finney ............... A61K 39/3955 |
| 2012/0076800 A1 | 3/2012 | Dai et al. |
| 2013/0071379 A1 | 3/2013 | Condra et al. |
| 2014/0186373 A1 | 7/2014 | Cosenza et al. |
| 2014/0220027 A1 | 8/2014 | Condra et al. |
| 2015/0093393 A1 | 4/2015 | Ma et al. |
| 2015/0307606 A1 | 10/2015 | Basarkar et al. |

FOREIGN PATENT DOCUMENTS

| JP | 2014-516953 A | 7/2014 | |
| WO | WO-03009817 A2 * | 2/2003 | ....... A61K 39/39591 |
| WO | 2005047327 A2 | 5/2005 | |
| WO | WO2005/047327 A2 | 5/2005 | |
| WO | 2007/124090 A1 | 11/2007 | |
| WO | 2007132480 A2 | 11/2007 | |
| WO | WO2007/132480 A2 | 11/2007 | |
| WO | 2009100318 A1 | 8/2009 | |
| WO | WO2009/100318 A1 | 8/2009 | |
| WO | WO-2010148337 A1 * | 12/2010 | ......... C07K 16/2887 |
| WO | 2012/15499 A1 | 2/2012 | |
| WO | 2012135408 A1 | 10/2012 | |
| WO | WO2012/135408 A1 | 10/2012 | |
| WO | 2013148686 A2 | 10/2013 | |
| WO | WO2013/148686 A2 | 10/2013 | |
| WO | 2014019727 A1 | 2/2014 | |
| WO | WO2014/019727 A1 | 2/2014 | |
| WO | 2015121318 A1 | 8/2015 | |
| WO | WO2015/121318 A1 | 8/2015 | |
| WO | 2016059512 A1 | 4/2016 | |
| WO | 2016/180765 A1 | 11/2016 | |

OTHER PUBLICATIONS

International Search Report issued in PCT/EP2017/061261, dated Aug. 4, 2017.
Kerwin, Bruce A., "Polysorbates 20 and 80 used in the formulation of protein biotherapeutics Structure and degradation pathways," Journal of Pharmaceutical Sciences 97:2924-2935 (2008).
Chang et al., "Effect of Sorbitol and Residential Moisture on the Stability of Lyophilized Antibodies: Implications for the Mechanism of Protein Stabilization in the Solid State," Journal of Pharmaceutical Sciences 94(7) 2005 pp. 1445-1455.
Muzammil, S. et al., "FcRn binding is not sufficient for achieving systemic therapeutic Tevels of immunoglobulin G after oral delivery of enteric-coated capsules in cynomolgus macaques," Pharmacology Research & Perspectives 4(3):e00218, pp. 1-17 (2016).

\* cited by examiner

*Primary Examiner* — Yunsoo Kim
(74) *Attorney, Agent, or Firm* — Medler Ferro Woodhouse & Mills

(57) ABSTRACT

The present invention relates to pharmaceutical compositions comprising an antibody or a fragment thereof suitable for freeze-drying (i.e. lyophilizing). The pharmaceutical compositions, which comprise an antibody or an antigen-binding fragment thereof; from 1% to 20% w/v sucrose; an amino acid or a mixture of amino acids; and surfactant, are provided as pharmaceutical compositions for freeze-drying; as freeze-dried (i.e. lyophilized) compositions which can be reconstituted into a solvent at the time of use or as reconstituted liquid formulations ready for administration.

12 Claims, 13 Drawing Sheets
Specification includes a Sequence Listing.

PHARMACEUTICAL COMPOSITION

FIELD OF THE INVENTION

The present invention belongs to the field of pharmaceutical formulations. More specifically, it relates to a pharmaceutical composition, liquid or freeze-dried, comprising an antibody, sucrose, an amino acid or a mixture of amino acids and a surfactant.

BACKGROUND OF THE INVENTION

The industrial manufacture of therapeutic antibodies is a complex task. It requires scale-up from processes developed in a laboratory for producing antibodies in milligram quantities to multi-kilogram quantities. Despite antibodies being fairly stable molecules, when stored at high concentration over a period of time they may, nevertheless, suffer from chemical and physical instability. Typical chemical instability may result in deamidation, hydrolysis, oxidation, beta-elimination, disulfide exchange or reduction. Physical instability can result in denaturation, aggregation or precipitation.

Whilst liquid formulations can be administered with minimal preparation, they have the drawback of being less stable over time. Liquid water-based formulations are particularly complex; water acts as a reactant or facilitates the transfer of reactants leading to chemical degradation and protein instability. The stabilization of proteins in liquid formulations to avoid or minimize aggregation, precipitation or degradation remains a particular challenge. Aggregation, with the formation of insoluble matter or precipitate, is a particular problem. This may cause various problems such as aggregates' formation which could lead to immunological reactions upon administration and/or difficulty in performing proper administration of the pharmaceutical formulation, e.g. by causing blockage of the delivery device.

Antibodies may be formulated in freeze-dried, i.e. lyophilized form for reconstitution in a solvent shortly before administration. Freeze-dried formulations of antibodies tend to be more stable than liquid water-based formulation. Freeze-drying facilitates achieving high concentrations of the antibody in the final formulation, thus, reducing the injection volume as well as the injection time.

In addition, freeze-drying (lyophilization) is the method of choice for long term storage stabilization of monoclonal antibodies that are otherwise unstable in liquid form. Freeze-drying antibodies at a lower temperature reduces the damage to the products and aids retaining molecular integrity. It extends the shelf life, reduces the temperature requirement for shipping and preserves the antibodies chemical and biological properties.

Antibodies, as other proteins, undergo denaturation upon freeze-drying in the absence of stabilizers. Different stabilizers such as sugars or polyols are normally added to the formulations to protect antibodies against degradation during freeze-drying and storage. The level of stabilization afforded by sugars or polyols generally depends on their concentrations. Increasing sugar/polyol concentration to a certain level may eventually reach a limit of stabilization or even destabilize a protein during freeze-drying, so a specific concentration of stabilizer to protein is required for storage stability of a freeze-dried antibody (Chang L, et al. J Pharm Sci. 2005; 94:1445-55). The level of stabilizers used for protection during freeze-drying depends on the formulation composition, concentration and physical properties of the stabilizer, and its compatibility with the antibody. The mechanism of stabilization during drying is that the stabilizer acts as a water substitute. The interaction between water and proteins is critical to the conformational stability of the proteins. When water is removed during drying, the stabilizers can form hydrogen bonds with the protein, as water molecules do, thereby preserve the native protein structure during lyophilization process (Chang L, et al. J Pharm Sci. 2005; 94:1445-55).

Despite lyophilization being a good choice to achieve the desired long term storage for antibodies, there is no simple, universal protocol in formulating antibodies. Antibodies can become unstable during lyophilization processes and/or long term storage, aggregates may form upon reconstitution or lyophilized cakes may take too long to reconstitute. High concentration of stabilizers may affect the physic-chemical properties (i.e. viscosities) of the final formulation.

Given the above, there remains a need in the art to provide further improved pharmaceutical compositions of antibodies suitable for freeze-drying.

SUMMARY OF THE INVENTION

The present invention addresses the above-identified need by providing pharmaceutical compositions comprising an antibody or a fragment thereof suitable for freeze-drying (i.e. lyophilizing). The resulting pharmaceutical compositions can be provided as freeze-dried (i.e. lyophilized) compositions which can be reconstituted into a solvent at the time of use or as reconstituted liquid formulations ready for administration. Reconstitution in reduced volumes allows achieving formulation with high concentrations of antibody or fragment thereof with a low level of aggregation and delivery time.

The following specific embodiments are described as numbered hereinafter:

1. A pharmaceutical composition comprising:
   a. an antibody or an antigen-binding fragment thereof;
   b. from 1% to 20% w/v sucrose;
   c. an amino acid or a mixture of amino acids; and
   d. a surfactant.
2. The pharmaceutical composition according to Embodiment 1, wherein having pH of from 4.0 to 7.5.
3. The pharmaceutical composition according to Embodiment 1 or Embodiment 2, wherein the antibody or antigen-binding fragment thereof is at a concentration of from 1 to 200 mg/mL, preferably from 50 to 150 mg/mL, more preferably from 80 to 140 mg/mL.
4. The pharmaceutical composition according to any one of the preceding Embodiments, wherein the composition comprises from 5% to 13% w/v sucrose, preferably from 7% to 10% w/v sucrose, more preferably 7% w/v sucrose.
5. The pharmaceutical composition according to any one of the preceding Embodiments, wherein:
   a. the amino acid is histidine or proline; or
   b. the mixture of amino acids comprises histidine and proline.
6. The pharmaceutical composition according to any one of the preceding Embodiments, wherein the composition comprises 0.01 to 1.0% w/v, preferably from 0.01% to 0.5% w/v of the surfactant.
7. The pharmaceutical composition according to Embodiment 6, wherein the surfactant is polysorbate 80.
8. The pharmaceutical composition according to any one of the preceding Embodiments, wherein the antibody or antigen-binding fragment thereof specifically binds human FcRn.

9. The pharmaceutical composition according to any one of the preceding Embodiments, wherein the antibody is a human or humanised antibody.
10. The pharmaceutical composition according to any one of the preceding Embodiments, wherein the antibody or antigen-binding fragment thereof comprises a light variable region as defined in SEQ ID NO: 7 and a heavy variable region as defined in SEQ ID NO: 8.
11. The pharmaceutical composition according to any one of the preceding Embodiments, wherein the composition comprises from 1 mg/mL to 200 mg/mL of antibody or antigen-binding fragment thereof, from 10 mM to 50 mM histidine, from 10 to 300 mM proline, from 1% to 20% w/v sucrose, from 0.01% to 1.0% w/v polysorbate 80, at pH 5.6; preferably the composition comprises from 50 mg/mL to 150 mg/mL of antibody or antigen-binding fragment thereof, from 20 mM to 40 mM histidine, from 50 to 280 mM proline, from 5% to 13% w/v sucrose, from 0.01% to 0.5% w/v polysorbate 80, at pH 5.6; more preferably the composition comprises from 80 mg/mL to 140 mg/mL of antibody or antigen-binding fragment thereof, 30 mM histidine, 180 mM proline, 7% w/v sucrose, 0.03% w/v polysorbate 80, at pH 5.6; and even more preferably the composition comprises 100 mg/mL of antibody or antigen-binding fragment thereof, 30 mM histidine, 180 mM proline, 7% w/v sucrose, 0.03% w/v polysorbate 80, at pH 5.6.
12. The pharmaceutical composition according to any one of the preceding Embodiments, wherein the composition further comprises mannitol and/or arginine and/or glycine.
13. A freeze-dried pharmaceutical composition comprising an antibody or an antigen-binding fragment thereof, sucrose, an amino acid or a mixture of amino acids, and optionally a surfactant.
14. The freeze-dried formulation according to Embodiment 13 wherein the formulation comprises from 10% to 40% w/w sucrose, preferably from 20% to 40% w/w sucrose.
15. A freeze-dried formulation comprising an antibody comprising a light variable region as defined in SEQ ID NO: 7 and a heavy variable region as defined in SEQ ID NO: 8 and from 10% to 40% w/w sucrose.
16. A liquid pharmaceutical formulation comprising the pharmaceutical composition according to any one of the Embodiments 13 to 15 and a solvent.
17. The liquid pharmaceutical formulation according to Embodiment 16, wherein the solvent is water.
18. A container comprising the freeze-dried formulation according to any one of Embodiments 13 to 15 or the liquid pharmaceutical formulation according to any one of Embodiments 16 or 17.
19. The pharmaceutical composition according to any one of Embodiments 1 to 12, the freeze-dried formulation according to any one of Embodiment 13 to 15 or the liquid pharmaceutical formulation according to any one of Embodiments 16 to 17 for use in therapy.
20. The pharmaceutical composition according to any one of Embodiments 1 to 12, the freeze-dried formulation according to any one of Embodiment 13 to 15 or the liquid pharmaceutical formulation according to any one of Embodiments 16 to 17 for use in the treatment of inflammatory or autoimmune diseases selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof.
21. A method for treating an inflammatory or autoimmune disease in a mammalian subject comprising administering pharmaceutical composition according to any one of Embodiments 1 to 12, the freeze-dried formulation according to any one of Embodiment 13 to 15 or the liquid pharmaceutical formulation according to any one of Embodiments 16 to 17; wherein the inflammatory or autoimmune disease is selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof.
22. A method for producing a pharmaceutical composition comprising an anti-FcRn antibody, wherein the method comprises the steps of:
    (i) preparing a composition comprising an anti-FcRn antibody; and
    (ii) adding 1% to 20% w/v sucrose.
23. The method according to Embodiment 22 wherein the pharmaceutical composition resulting from step (ii) is a pharmaceutical composition according to any one of Embodiments 1 to 12.
24. The method according to Embodiment 22 or Embodiment 23, wherein the method further comprises the step of freeze-drying the pharmaceutical composition resulting from step (ii).
25. The pharmaceutical composition obtained by the method according to Embodiment 24.
26. A method for reconstituting a pharmaceutical composition according to any one of Embodiments 13, 14, 15, 24 or 25 by adding a solvent, wherein the solvent is preferably water.
27. A liquid pharmaceutical formulation obtained by the method according to Embodiment 26.

DETAILED DESCRIPTION OF THE INVENTION

Figure 1:
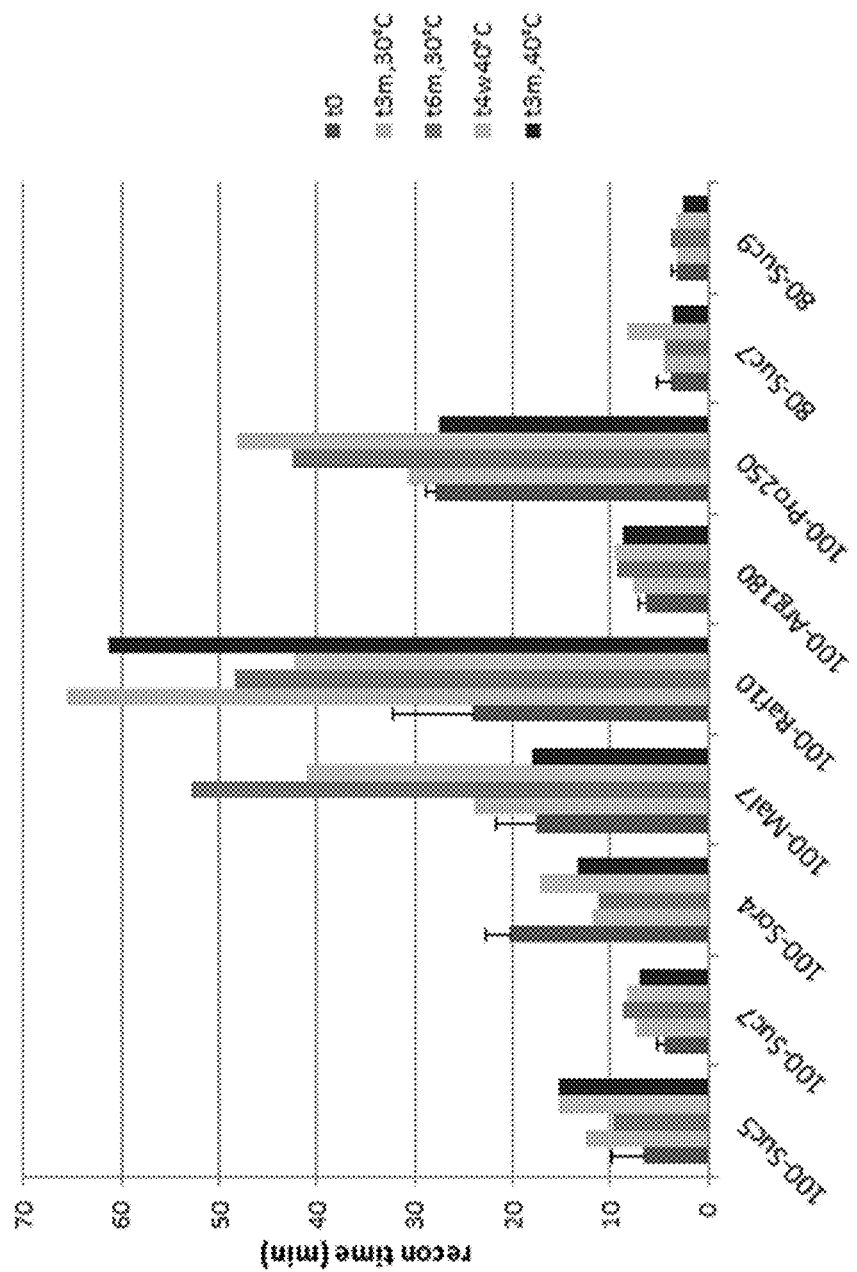
FIG. 1. Reconstitution time upon lyophilisation. Reconstitution time (recon time) is shown on the y-axis in minutes per each of the formulations (x-axis) of Table 2.

The pharmaceutical composition according to the invention comprises an antibody or an antigen binding fragment thereof; from 1% to 20% w/v sucrose; an amino acid or a mixture of amino acids; and a surfactant.

The concentration of antibody or antigen-binding fragment thereof in the pharmaceutical composition may be from 1 to 200 mg/mL, preferably from 50 to 200 mg/mL, more preferably from 80 to 140 mg/mL.

Preferably the antibody or antigen-binding fragment thereof comprised in the pharmaceutical composition according to the invention specifically binds to human FcRn.

The term "specifically binds to human FcRn", "specifically binding to human FcRn", and equivalents as used herein means the antibody will bind to human FcRn with sufficient affinity and specificity to achieve a biologically meaningful effect. The antibody selected will normally have a binding affinity for human FcRn, for example, the antibody may bind human FcRn with a Kd value of between 100 nM and 1 pM. Antibody affinities may be determined for example by a surface plasmon resonance bases assay, such as the BIAcore assay; enzyme-linked immunoabsorbent assay (ELISA); and competition assays (e.g. RIA's). Within the meaning of the present invention an antibody or antigen-binding fragment thereof specifically binding to human FcRn may also bind to another molecule, e.g. cyno FcRn or such as by way of a non-limiting example in the case of a bispecific antibody.

FcRn is a non-covalent complex of membrane protein FcRn α chain and β2 microglobulin (β2M). In adult mammals FcRn plays a key role in maintaining serum antibody levels by acting as a receptor that binds and salvages antibodies of the IgG isotype. IgG molecules are endocytosed by endothelial cells, and if they bind to FcRn, are recycled transcytosed out into, for example circulation. In contrast, IgG molecules that do not bind to FcRn enter the cells and are targeted to the lysosomal pathway where they are degraded. A variant IgG1 in which His435 is mutated to alanine results in the selective loss of FcRn binding and a significantly reduced serum half-life (Firan et al. 2001, International Immunology 13:993).

The antibody or antigen-binding fragment thereof binding specifically to human FcRn, preferably also neutralizes human FcRn.

The term "neutralizes" as used herein refers to an antibody that inhibits or substantially reduces the biological effect of the molecule to which it specifically binds. Therefore, the expression "the antibody neutralizes human FcRn" refers to an antibody that specifically binds to human FcRn and inhibits or substantially reduces the biological effect thereof such as by blocking FcRn binding to IgG.

The term "antibody" or "antibodies" as used herein refers to monoclonal or polyclonal antibodies and is not limited to recombinant antibodies that are generated by recombinant technologies as known in the art.

Preferably, the antibody comprised in the pharmaceutical composition according to the invention is a monoclonal antibody which specifically binds human FcRn.

"Antibody" or "antibodies" include antibodies' of any species, in particular of mammalian species, having two essentially complete heavy and two essentially complete light chains, human antibodies of any isotype, including $IgA_1$, $IgA_2$, IgD, $IgG_1$, $IgG_{2a}$, $IgG_{2b}$, $IgG_3$, $IgG_4$ IgE and IgM and modified variants thereof, non-human primate antibodies, e.g. from chimpanzee, baboon, rhesus or cynomolgus monkey, rodent antibodies, e.g. from mouse, rat or rabbit; goat or horse antibodies, and derivatives thereof, or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region or complementarity determining region (CDR) of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human diseases. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. The term "antibody" or "antibodies" as used herein, also refers to an aglycosylated antibody.

The term "antigen-binding fragment thereof" or grammatical variations thereof as used herein refers to an antibody fragment. A fragment of an antibody comprises at least one heavy or light chain immunoglobulin domain as known in the art and binds to one or more antigen(s). Examples of antibody fragments according to the invention include Fab, Fab', F(ab')$_2$, and Fv and scFv fragments; as well as diabodies, triabodies, tetrabodies, minibodies, domain antibodies (dAbs), such as sdAbs, VHH or camelid antibodies (e.g. from camels or llamas such as Nanobodies™) and VNAR fragments, single-chain antibodies, bispecific, trispecific, tetraspecific or multispecific antibodies formed from antibody fragments or antibodies, including but not limited to Fab-Fv or Fab-Fv-Fv constructs. Antibody fragments as defined above are known in the art.

The antibody or antigen-binding fragment thereof comprised in the pharmaceutical composition according to the invention may be a human or humanized antibody, preferably a humanized monoclonal antibody which specifically binds human FcRn.

More preferably the pharmaceutical composition according to the invention comprises (Table 1):

1) an antibody or antigen-binding fragment thereof which
   a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
   b. comprises a light variable region having the sequence as defined in SEQ ID NO: 7 and a heavy variable region having the sequence as defined in SEQ ID NO: 8; or
   c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
   d. comprises a light variable region having the sequence as defined in SEQ ID NO: 7 and a heavy chain having the sequence as defined in SEQ ID NO: 11; or
   e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or
2) an antibody which comprises a light chain having the sequence as defined in SEQ ID NO: 9 and a heavy chain having the sequence as defined in SEQ ID NO: 10; or
3) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

Throughout this specification, complementarity determining regions ("CDR") are defined according to the Kabat definition. The Kabat definition is a standard for numbering the residues in an antibody and it is typically used to identify CDR regions (Kabat et al., (1991), 5th edition, NIH publication No. 91-3242).

TABLE 1

| Region and SEQ ID identifier | Amino acid sequence |
|---|---|
| CDR-H1 SEQ ID NO: 1 | GFTFSNYGMV |
| CDR-H2 SEQ ID NO: 2 | YIDSDGDNTYYRDSVKG |
| CDR-H3 SEQ ID NO: 3 | GIVRPFLY |
| CDR-L1 SEQ ID NO: 4 | KSSQSLVGASGKTYLY |
| CDR-L2 SEQ ID NO: 5 | LVSTLDS |
| CDR-L3 SEQ ID NO: 6 | LQGTHFPHT |
| Light variable region SEQ ID NO: 7 | DIQMTQSPSS LSASVGDRVT ITCKSSQSLV GASGKTYLYW LFQKPGKAPK RLIYLVSTLD SGIPSRFSGS GSGTEFTLTI SSLQPEDFAT YYCLQGTHFP HTFGQGTKLE IK |
| Heavy variable region SEQ ID NO: 8 | EVPLVESGGG LVQPGGSLRL SCAVSGFTFS NYGMVWVRQA PGKGLEWVA IDSDGDNTYY RDSVKGRFTI SRDNAKSSLY LQMNSLRAED TAVYYCTTG VRPFLYWGQG TLVTVS |

TABLE 1-continued

| Region and SEQ ID identifier | Amino acid sequence |
|---|---|
| Light chain SEQ ID NO: 9 | DIQMTQSPSS LSASVGDRVT ITCKSSQSLV GASGKTYLYW LFQKPGKAPK RLIYLVSTLD SGIPSRFSGS GSGTEFTLTI SSLQPEDFAT YYCLQGTHFP HTFGQGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| Heavy chain SEQ ID NO: 10 | EVPLVESGGG LVQPGGSLRL SCAVSGFTFS NYGMVWVRQA PGKGLEWVAY IDSDGDNTYY RDSVKGRFTI SRDNAKSSLY LQMNSLRAED TAVYYCTTGI VRPFLYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |
| Fab heavy chain SEQ ID NO: 11 | EVPLVESGGG LVQPGGSLRL SCAVSGFTFS NYGMVWVRQA PGKGLEWVA IDSDGDNTYY RDSVKGRFTI SRDNAKSSLY LQMNSLRAED TAVYYCTTG VRPFLYWGQG TLVTVSSAST KGPSVFPLAP SSKSTSGGTA ALGCLVKDY PEPVTVSWNS GALTSGVHTF PAVLQSSGLY SLSSVVTVPS SSLGTQTYI NVNHKPSNTK VDKKVEPKSC |

The antibody or antigen binding fragment thereof exemplified is further described in details in WO2014019727 (incorporated herein by reference).

Antibody molecules may be typically produced by culturing a host cell containing a vector encoding the antibody sequence under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

An antibody or an antigen-binding fragment thereof that can be manufactured according to industrial scales can be produced by culturing eukaryotic host cells transfected with one or more expression vectors encoding the recombinant antibody fragment. The eukaryotic host cells are preferably mammalian cells, more preferably Chinese Hamster Ovary (CHO) cells.

Mammalian cells may be cultured in any medium that will support their growth and expression of the recombinant protein, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody or antibody fragment.

An antibody or antigen-binding fragment thereof is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation.

Therefore, the antibody or antigen-binding fragment thereof production method comprises a step of centrifugation and supernatant recovery after cell culture and prior to protein purification. In a further particular embodiment said centrifugation is continuous centrifugation. For avoidance of doubt, supernatant denotes the liquid lying above the sedimented cells resulting from the centrifugation of the cell culture.

Alternatively, host cells are prokaryotic cells, preferably gram-negative bacteria. More preferably, the host cells are *E. coli* cells. Prokaryotic host cells for protein expression are well known in the art (Terpe, K. Appl Microbiol Biotechnol 72, 211-222 (2006)). The host cells are recombinant cells which have been genetically engineered to produce the protein of interest such as an antigen-binding fragment of an antibody. The recombinant *E. coli* host cells may be derived from any suitable *E. coli* strain including from MC4100, TG1, TG2, DHB4, DH5α, DH1, BL21, K12, XL1Blue and JM109. One example is *E. coli* strain W3110 (ATCC 27,325) a commonly used host strain for recombinant protein fermentations. Antibody fragments can also be produced by culturing modified *E. coli* strains, for example metabolic mutants or protease deficient *E. coli* strains.

An antibody fragment is typically found in either the periplasm of the E. coli host cell or in the host cell culture supernatant, depending on the nature of the protein, the scale of production and the E. coli strain used. The methods for targeting proteins to these compartments are well known in the art (Makrides, S. C.; Microbiol Rev 60, 512-538 (1996)). Examples of suitable signal sequences to direct proteins to the periplasm of E. coli include the E. coli PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, the recombinant protein is expressed in the periplasm of the host E. coli.

Expression of the recombinant protein in the E. coli host cells may also be under the control of an inducible system, whereby the expression of the recombinant antibody in E. coli is under the control of an inducible promoter. Many inducible promoters suitable for use in E. coli are well known in the art and depending on the promoter expression of the recombinant protein can be induced by varying factors such as temperature or the concentration of a particular substance in the growth medium. Examples of inducible promoters include the E. coli lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

E. coli host cell cultures (fermentations) may be cultured in any medium that will support the growth of E. coli and expression of the recombinant protein. The medium may be any chemically defined medium such as e.g. described in Durany O, et al. (2004). Studies on the expression of recombinant fuculose-1-phosphate aldolase in Escherichia coli. Process Biochem 39, 1677-1684.

Culturing of the E. coli host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Fermentation of E. coli may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the E. coli host cells and to allow higher cell densities to be reached.

If desired, the host cells may be subject to collection from the fermentation medium, e.g. host cells may be collected from the sample by centrifugation, filtration or by concentration. In this case the process typically comprises a step of centrifugation and cell recovery prior to extracting the protein.

For E. coli fermentation processes wherein the protein of interest such as an antibody or antigen-binding fragment of an antibody is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art. Therefore in a particular embodiment, the production process comprises an additional protein extraction step prior to protein purification.

Other methods for obtaining antigen-binding fragment of a human antibody in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody.

The pharmaceutical composition according to the invention may have a pH of 4.0 to 7.5, preferably of 4.0 to 6.0, more preferably 4.5 to 6.0, even more preferably from 5.5 to 5.8 or most preferred about 5.6.

The pharmaceutical composition contains a buffering agent to maintain the pH constant. There are many buffering agents used in the field of liquid pharmaceutical formulations, such as, but not limited to, citrate, phosphate, lactate, histidine, glutamate, maleate, tartrate, or succinate. A preferred buffer species is typically selected amongst those having a pKa that is close (+/−1 pH unit) to the preferred pH for optimal protein stability in order to maintain high buffering capacity, and is associated with the maximal demonstrated stability observed for a particular protein when placed in a series of varied buffer species. The adequate pH ranges of a formulation are generally chosen from those associated with the maximal demonstrated stability observed for a particular protein when placed in a series of varied pH formulations.

The pharmaceutical composition according to the invention comprises as a buffering agent, an amino acid or a mixture of amino acids, preferably at a concentration of 10 mM to 100 mM, 10 mM to 80 mM, 10 mM to 60 mM, 25 mM to 60 mM, preferably 30 mM to 50 mM, or 30 mM.

Suitable amino acids are arginine, lysine, histidine, methionine, ornithine, isoleucine, leucine, alanine, glycine, glutamic acid or aspartic acid. The inclusion of a basic amino acid is preferred i.e. arginine, lysine and/or histidine. An amino acid may be present in its D- and/or L-form, but the L-form is typical. The amino acid may be present as any suitable salt e.g. a hydrochloride salt, such as arginine-HCl.

Preferably the amino acid is histidine, more preferably at a concentration of 30 mM.

The pharmaceutical composition according to the invention may also comprise a mixture of amino acids for example a mixture of histidine and proline, histidine, proline and glycine, histidine, proline and arginine, histidine, proline, arginine and glycine. Preferably, the pharmaceutical composition according to the invention comprises histidine and another amino acid, preferably proline at a concentration of 10 mM to 300 mM, 50 mM to 280 mM, 100 mM to 280 mM or 180 mM to 250 mM. Preferably, the pharmaceutical composition according to the invention comprises 30 mM histidine and from 180 mM to 250 mM proline.

The pharmaceutical composition according to the invention additionally comprises a surfactant. Surfactants available for use in the pharmaceutical composition according to invention include, but are not limited to, non-ionic surfactants, ionic surfactants and zwitterionic surfactants. Typical surfactants for use with the invention include, but are not limited to, sorbitan fatty acid esters (e.g. sorbitan monocaprylate, sorbitan monolaurate, sorbitan monopalmitate), sorbitan trioleate, glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils {e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearic acid amide); $C_{10}$-$C_{18}$ alkyl sulfates (e.g. sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g. sodium polyoxyethylene lauryl sulfate), and $C_1$-$C_{18}$ alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of $C_{12}$-$C_{18}$ fatty acids. The composition may include one or more of these surfactants. Preferred surfactants are polyoxyethylene sorbitan fatty acid esters e.g. polysorbate 20, 40, 60 or 80. Preferably the pharmaceutical composition according to the invention comprises polysorbate 80.

The pharmaceutical composition of the invention may comprise from 0.01% to 10% w/v of surfactant, from 0.01% to 1.0% w/v of surfactant, from 0.01% to 0.5% w/v of surfactant or 0.03% w/v of surfactant such as polysorbates. Preferably, the pharmaceutical composition of the invention comprises 0.03% w/v of polysorbate 80.

The pharmaceutical composition according to the present invention comprises as a stabilizer (i.e. cryoprotectant) from 1 to 20% w/v, or from 5% to 13% w/v or from 7% to 10% w/v or 7% of sucrose.

The present invention also provides for a method for producing a pharmaceutical composition comprising an anti-FcRn antibody or antigen-binding fragment thereof, whereby the method comprises preparing a composition comprising an anti-FcRn antibody, for example a composition comprising from 80 mg/mL to 140 mg/mL of an anti-FcRn antibody or antigen-binding fragment thereof comprising a light variable chain comprising SEQ ID NO: 7 and a heavy variable chain comprising SEQ ID NO:8, 30 mM histidine, 250 mM proline, 0.03% w/v polysorbate 80, at pH 5.6, and adding 1% to 25% w/v of sucrose.

Preferably, the method comprises preparing a composition comprising from 80 mg/mL to 140 mg/mL of an anti-FcRn antibody comprising a light variable chain comprising SEQ ID NO: 7 and a heavy variable chain comprising SEQ ID NO:8, 30 mM histidine, 250 mM proline, 0.03% w/v polysorbate 80, at pH 5.6, and adding a composition comprising 30 mM histidine, 0.03% w/v polysorbate 80, from 17.5% to 24.5% w/v of sucrose at pH 5.6.

The pharmaceutical compositions described and embodied herein may be in the form of a freeze-dried (i.e. lyophilized) pharmaceutical composition.

Hence, the method for producing a pharmaceutical composition according to the invention may further comprise the step of freeze-drying (i.e. lyophilizing).

Techniques for lyophilization of antibodies are well known in the art (John F. Carpenter and Michael J. Pikal, 1997 Pharm. Res. 14, 969-975); similarly there are available our days monoclonal antibody products such as SYNAGIS™, REMICADE™, RAPTIVA™, SIMULECT™, XOLAIR™ and HERCEPTIN™ which are supplied as lyophilizates. These antibodies are reconstituted to various final concentrations e.g. SIMULECT™ is reconstituted to a concentration of 4 mg/ml antibody, REMICADE™ is reconstituted to a concentration of 10 mg/ml, HERCEPTIN™ to 21 mg/ml, SYNAGIS™ and RAPTIVA™ to 100 mg/ml, and XOLAIR™ to 125 mg/ml.

Freeze-drying techniques will be discussed further herein the example section.

The present invention, therefore, provides for a freeze-dried formulation comprising an antibody or antigen-binding fragment thereof, sucrose, an amino acid or a mixture of amino acids and optionally a surfactant. Preferably the freeze-dried formulation comprises from 10% to 40% w/w sucrose, more preferably from 20% to 40% w/w sucrose.

In a preferred embodiment of the present invention the freeze-dried formulation comprising 10% to 40% w/w of sucrose also comprises an anti-FcRn antibody or antigen-binding fragment thereof wherein the antibody or fragment thereof comprises a light variable chain comprising SEQ ID NO:7 and a heavy variable chain comprising SEQ ID NO:8.

In another preferred embodiment, the freeze-dried formulation comprises about 50.8% w/w of antibody or antigen-binding fragment thereof, about 35.5% w/w/sucrose, about 3.0% w/w histidine, about 10.5% w/w proline and 0.2% w/w polysorbate 80; wherein the antibody or fragment thereof comprises a light variable chain comprising SEQ ID NO:7 and a heavy variable chain comprising SEQ ID NO:8.

Additional excipients for use within the pharmaceutical compositions according to the invention include, but are not limited to, viscosity enhancing agents, bulking agents, solubilising agents such as monosaccharides, e.g., fructose, maltose, galactose, glucose, D-mannose, sorbose and the like; disaccharides, e.g. lactose, trehalose, cellobiose, and the like; polysaccharides, e.g. raffinose, melezitose, maltodextrins, dextrans, starches, and the like; and polyols, such as mannitol, xylitol, maltitol, lactitol, xylitol sorbitol (glucitol) and the like; poly-ethylene glycols (e.g. PEG100, PEG300, PEG600, PEG1500, PEG2000, PEG3000, PEG3350, PEG4000, PEG6000, PEG8000 or PEG20000), polyvinylpyrrolidone, trimethylamine N-oxide, trimethylglycine or combinations thereof.

Before a freeze-dried (i.e. lyophilized) pharmaceutical composition can be administered to a patient it needs to be reconstituted with a solvent. Within the present invention, the preferred solvent is an aqueous solvent, more preferably the aqueous solvent is water.

The volume of solvent used for reconstitution dictates the concentration of the antibody or antigen-binding fragment thereof in the resulting liquid pharmaceutical formulation. Reconstitution with a smaller volume of solvent than the pre-lyophilization volume provides a formulation which is more concentrated than before lyophilization and vice-versa.

The present invention therefore provides for a method for reconstituting a freeze-dried pharmaceutical composition according to the invention by adding a solvent, wherein the solvent is preferably water.

The reconstitution ratio (volume of pre-lyophilized pharmaceutical composition to solvent used to reconstitute the freeze-dried pharmaceutical composition) may vary from 0.5:1 to 1:10. In a preferred embodiment, a ratio of about 1:1 is applied so that the resulting volume of the reconstituted liquid pharmaceutical formulation is about 4.4 mL.

Preferred pharmaceutical compositions pre-lyophilization and/or reconstituted liquid pharmaceutical formulations according to the invention comprise:

A. from 1 mg/mL to 200 mg/mL of an antibody or antigen-binding fragment thereof comprising a light variable chain comprising SEQ ID NO: 7 and a heavy variable chain comprising SEQ ID NO:8, from 10 mM to 50 mM histidine, from 10 to 300 mM proline, from 1% to 20% w/v sucrose, from 0.01% to 1.0% w/v polysorbate 80, at pH 5.6;

B. from 50 mg/mL to 150 mg/mL of an antibody or antigen-binding fragment thereof comprising a light variable chain comprising SEQ ID NO: 7 and a heavy variable chain comprising SEQ ID NO:8, from 20 mM to 40 mM histidine, from 50 to 280 mM proline, from 5% to 13% w/v sucrose, from 0.01% to 0.5% w/v polysorbate 80, at pH 5.6;

C. from 80 mg/mL to 140 mg/mL of an antibody or antigen-binding fragment thereof comprising a light variable chain comprising SEQ ID NO: 7 and a heavy variable chain comprising SEQ ID NO:8, 30 mM histidine, 250 mM proline, 7% w/v sucrose, 0.03% w/v polysorbate 80, at pH 5.6;

D. from 50 mg/mL to 150 mg/mL of an antibody or antigen-binding fragment thereof comprising a light variable chain comprising SEQ ID NO: 7 and a heavy variable chain comprising SEQ ID NO:8 or a heavy chain comprising SEQ ID NO:11, 30 mM histidine, 180 mM proline, 7% w/v sucrose, 0.03% w/v polysorbate 80, at pH 5.6;

E. from 80 mg/mL to 140 mg/mL, preferably 100 mg/ml, of antibody or antigen-binding fragment thereof comprising a heavy variable chain and a light variable chain, wherein the heavy variable chain comprises CDR-H1 of SEQ ID NO:1, CDR-H2 of SEQ ID NO:2 and CDR-H3 of SEQ ID NO:3 and the light variable chain comprises CDR-L1 of SEQ ID NO:4, CDR-L2 of SEQ ID NO:5 and CDR-L3 of SEQ ID NO:6, 30 mM histidine, 180 mM proline, 7% w/v sucrose, 0.03% w/v polysorbate 80, at pH 5.6;

F. from 80 mg/mL to 140 mg/mL, preferably 100 mg/ml, of antibody comprising a heavy chain comprising SEQ ID NO: 10 and a light chain comprising SEQ ID NO:9, 30 mM histidine, 180 mM proline, 7% w/v sucrose, 0.03% w/v polysorbate 80, at pH 5.6 and at least i) or i) and ii) or i), ii) and iii):
  i) from 100 mM to 250 mM of mannitol;
  ii) from 80 mM to 200 mM of L-arginine HCl;
  iii) from 100 mM to 280 mM of glycine;

G. from 80 mg/mL to 140 mg/mL, preferably 100 mg/ml, of an antibody or antigen-binding fragment thereof comprising a light variable chain comprising SEQ ID NO: 7 and a heavy variable chain comprising SEQ ID NO:8 or a heavy chain comprising SEQ ID NO:11, 30 mM histidine, 180 mM proline, 7% w/v sucrose, 0.03% w/v polysorbate 80, at pH 5.6 and at least i) or i) and ii) or i), ii) and iii):
  i) from 100 mM to 250 mM of mannitol;
  ii) from 80 mM to 200 mM of L-arginine HCl;
  iii) from 100 mM to 280 mM of glycine;

H. from 80 mg/mL to 140 mg/mL, preferably 100 mg/ml, of an antibody or antigen-binding fragment thereof comprising a heavy variable chain and a light variable chain, wherein the heavy variable chain comprises CDR-H1 of SEQ ID NO:1, CDR-H2 of SEQ ID NO:2 and CDR-H3 of SEQ ID NO:3 and the light variable chain comprises CDR-L1 of SEQ ID NO:4, CDR-L2 of SEQ ID NO:5 and CDR-L3 of SEQ ID NO:6, 30 mM histidine, 180 mM proline, 7% w/v sucrose, 0.03% w/v polysorbate 80, at pH 5.6 and at least i) or i) and ii) or i), ii) and iii):
  i) from 100 mM to 250 mM of mannitol;
  ii) from 80 mM to 200 mM of L-arginine HCl;
  iii) from 100 mM to 280 mM of glycine;

I. from 80 mg/mL to 140 mg/mL, preferably 100 mg/ml, of an antibody comprising a heavy chain comprising SEQ ID NO: 10 and a light chain comprising SEQ ID NO:9, 30 mM histidine, 180 mM proline, 7% w/v sucrose, 0.03% w/v polysorbate 80, at pH 5.6 and at least i) or i) and ii) or i), ii) and iii):
  i) from 100 mM to 250 mM of mannitol;
  ii) from 80 mM to 200 mM of L-arginine HCl;
  iii) from 100 mM to 280 mM of glycine;

The present invention also provides for a container comprising the freeze-dried pharmaceutical composition or the reconstituted liquid pharmaceutical formulation according to the invention. In particular, the container may be a vial comprising the freeze-dried pharmaceutical composition to be reconstituted.

The container may be part of a kit-of-parts comprising one or more containers comprising the freeze-dried pharmaceutical compositions according to the invention, suitable solvents for reconstituting the freeze-dried pharmaceutical composition, delivery devices such as a syringes and instructions of use.

The pharmaceutical compositions or the liquid pharmaceutical formulations according to the invention are for use in therapy.

In a preferred embodiment, the reconstituted liquid pharmaceutical formulation for use in therapy comprises from 80 mg/mL to 140 mg/mL, preferably 100 mg/ml, of an antibody or antigen-binding fragment thereof, 30 mM histidine, 180 mM proline, 7% w/v sucrose, 0.03% w/v polysorbate 80, at pH 5.6 optionally, i) or i) and ii) or i), ii) and iii) wherein:
  i) from 100 mM to 250 mM of mannitol;
  ii) from 80 mM to 200 mM of L-arginine HCl;
  iii) from 100 mM to 280 mM of glycine;
wherein the antibody or antigen-binding fragment thereof (as it may apply) comprises:
  1) a light variable chain comprising SEQ ID NO: 7 and a heavy variable chain comprising SEQ ID NO:8 or a heavy chain comprising SEQ ID NO:11; or
  2) a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
  3) a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11;
  4) a light chain comprising SEQ ID NO: 9 and a heavy chain comprising SEQ ID NO:10; or
  5) a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10;
  6) a heavy variable chain and a light variable chain, wherein the heavy variable chain comprises CDR-H1 of SEQ ID NO:1, CDR-H2 of SEQ ID NO:2 and CDR-H3 of SEQ ID NO:3 and the light variable chain comprises CDR-L1 of SEQ ID NO:4, CDR-L2 of SEQ ID NO:5 and CDR-L3 of SEQ ID NO:6.

The pharmaceutical composition or the liquid pharmaceutical formulations according to the invention are also for use in the treatment of inflammatory or autoimmune diseases selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof.

In another preferred embodiment, the reconstituted liquid pharmaceutical formulation for use in the treatment of inflammatory or autoimmune diseases selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof comprises from 80 mg/mL to 140 mg/mL, preferably 100 mg/ml, of an antibody or antigen-binding fragment thereof, 30 mM histidine, 180 mM proline, 7% w/v sucrose, 0.03% w/v polysorbate 80, at pH 5.6, optionally, i) or i) and ii) or i), ii) and iii) wherein:
  i) from 100 mM to 250 mM of mannitol;
  ii) from 80 mM to 200 mM of L-arginine HCl;
  iii) from 100 mM to 280 mM of glycine;
wherein the antibody or antigen-binding fragment thereof (as it may apply) comprises:
  1) a light variable chain comprising SEQ ID NO: 7 and a heavy variable chain comprising SEQ ID NO:8 or a heavy chain comprising SEQ ID NO:11; or
  2) a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
  3) a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11;
  4) a light chain comprising SEQ ID NO: 9 and a heavy chain comprising SEQ ID NO:10; or
  5) a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10;
  6) a heavy variable chain and a light variable chain, wherein the heavy variable chain comprises CDR-H1 of SEQ ID NO:1, CDR-H2 of SEQ ID NO:2 and CDR-H3 of SEQ ID NO:3 and the light variable chain comprises CDR-L1 of SEQ ID NO:4, CDR-L2 of SEQ ID NO:5 and CDR-L3 of SEQ ID NO:6.

The invention also provides for a method for treating an inflammatory or autoimmune disease in a mammalian subject comprising administering the pharmaceutical composition or the liquid pharmaceutical formulations according to the invention; wherein the inflammatory or autoimmune disease is selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof.

The mammalian subject may be selected from the group of rodents, cats, dogs, horses, bovine, ovine, non-human primates and human subjects. Preferably, the mammalian subject is a human subject.

In yet another preferred embodiment the method for treating an inflammatory or autoimmune disease in a mammalian subject comprising administering the reconstituted liquid pharmaceutical formulation comprising from 80 mg/mL to 140 mg/mL, preferably 100 mg/ml, of an antibody or antigen-binding fragment thereof, 30 mM histidine, 180 mM proline, 7% w/v sucrose, 0.03% w/v polysorbate 80, at pH 5.6, optionally, i) or i) and ii) or i), ii) and iii) wherein:
  iv) from 100 mM to 250 mM of mannitol;
  i) from 80 mM to 200 mM of L-arginine HCl;
  ii) from 100 mM to 280 mM of glycine;
wherein the antibody or antigen-binding fragment thereof (as it may apply) comprises:
  1) a light variable chain comprising SEQ ID NO: 7 and a heavy variable chain comprising SEQ ID NO:8 or a heavy chain comprising SEQ ID NO:11; or
  2) a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
  3) a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11;

4) a light chain comprising SEQ ID NO: 9 and a heavy chain comprising SEQ ID NO:10; or
5) a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10;
6) a heavy variable chain and a light variable chain, wherein the heavy variable chain comprises CDR-H1 of SEQ ID NO:1, CDR-H2 of SEQ ID NO:2 and CDR-H3 of SEQ ID NO:3 and the light variable chain comprises CDR-L1 of SEQ ID NO:4, CDR-L2 of SEQ ID NO:5 and CDR-L3 of SEQ ID NO:6.

and wherein the inflammatory or autoimmune disease is selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof.

Furthermore, the pharmaceutical composition or the liquid pharmaceutical formulations according to the invention may be used in the manufacture of a medicament for the treatment of inflammatory or autoimmune diseases selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof.

In another preferred embodiment, the reconstituted liquid pharmaceutical formulation may be used in the manufacture of a medicament for the treatment of inflammatory or autoimmune diseases selected from myasthenia gravis, Pemphigus vulgaris, Neuromyelitis optica, Guillain-Barré syndrome, lupus, and thrombotic thrombocytopenic purpura, Idiopathic thrombocytopenic purpura (ITP), Chronic inflammatory demyelinating polyneuropathy (CIDP) and combinations thereof comprises from 80 mg/mL to 140 mg/mL, preferably 100 mg/ml, of an antibody or antigen-binding fragment thereof, 30 mM histidine, 180 mM proline, 7% w/v sucrose, 0.03% w/v polysorbate 80, at pH 5.6, optionally, i) or i) and ii) or i), ii) and iii) wherein:
v) from 100 mM to 250 mM of mannitol;
vi) from 80 mM to 200 mM of L-arginine HCl;
vii) from 100 mM to 280 mM of glycine;
wherein the antibody or antigen-binding fragment thereof (as it may apply) comprises:
1) a light variable chain comprising SEQ ID NO: 7 and a heavy variable chain comprising SEQ ID NO:8 or a heavy chain comprising SEQ ID NO:11; or
2) a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
3) a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11;
4) a light chain comprising SEQ ID NO: 9 and a heavy chain comprising SEQ ID NO:10; or
5) a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10;
6) a heavy variable chain and a light variable chain, wherein the heavy variable chain comprises CDR-H1 of SEQ ID NO:1, CDR-H2 of SEQ ID NO:2 and CDR-H3 of SEQ ID NO:3 and the light variable chain comprises CDR-L1 of SEQ ID NO:4, CDR-L2 of SEQ ID NO:5 and CDR-L3 of SEQ ID NO:6.

The reconstituted liquid pharmaceutical formulations according to the invention are administered in a therapeutically effective amount. The term "therapeutically effective amount" as used herein refers to an amount of a therapeutic agent (i.e. an antibody) needed to treat, ameliorate or prevent a targeted disease, disorder or condition, or to exhibit a detectable therapeutic, pharmacological or preventative effect. For any antibody or antigen-binding fragments thereof, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount of antibody will be from 0.01 mg/kg to 500 mg/kg, for example 0.1 mg/kg to 200 mg/kg, such as 100 mg/kg.

For the treatment of the above diseases and/or disorders, the appropriate dosage will vary depending upon, for example, the particular antibody to be employed, the subject treated, the mode of administration and the nature and severity of the condition being treated. In a particular embodiment, the reconstituted liquid pharmaceutical formulation of the invention is administered by intravenous or subcutaneous route. When administered via intravenous injection, it may be administered as a bolus injection or as a continuous infusion. The reconstituted liquid pharmaceutical formulation according to any of the embodiments of the invention may also be administered by intramuscular injection. The reconstituted liquid pharmaceutical formulation may be injected using a syringe, an injection device such as an autoinjector, a needleless device, an implant and a patch.

In one specific embodiment of the present invention, a dosage of 400 mg is achieved by administering 4 mL of the 1:1 reconstituted liquid pharmaceutical formulation comprising 100 mg/mL of anti-FcRn antibody of antigen-binding fragment thereof.

The liquid pharmaceutical formulation of the invention is suitably administered to the patient at one time or over a series of treatments and may be administered to the patient at any time from diagnosis onwards; it may be administered as the sole treatment or in conjunction with other drugs or therapies useful in treating the conditions as described herein before.

The antibody or antigen-binding fragment thereof may be the sole active ingredient in the liquid pharmaceutical formulation. Alternatively, the antibody or antigen-binding fragment thereof may be administered in combination, e.g. simultaneously, sequentially or separately, with one or more other therapeutically active ingredients. Active ingredient as employed herein refers to an ingredient with a pharmacological effect, such as a therapeutic effect, at a relevant dose. In some embodiments the antibody or antigen-binding fragment thereof in the liquid pharmaceutical formulation may be accompanied by other active ingredients including other antibodies or non-antibody ingredients. When the antibody in the liquid pharmaceutical formulation according to the invention is an anti-FcRn antibody, the subject may be administered with an additional active ingredient to treat inflammatory or autoimmune disease. In one embodiment, the subject is administered, simultaneously or in sequence (before and/or after) other antibody ingredients or non-antibody ingredients such as steroids or other drug molecules, in particular drug molecules whose half-life is independent of FcRn binding.

The invention will now be further described by way of examples with references to embodiments illustrated in the accompanying drawings

EXAMPLES

Abbreviations

DLS (Dynamic Light Scattering); Arg (L-arginine); iCE (Imaged capillary electrophoresis); Mal (Maltitol); Pro (L-Proline); PS80 (Polysorbate 80); Raf (Raffinose); SE-UPLC (Size-exclusion Ultra Performance Liquid Chromatography); Sor (Sorbitol); Suc (Sucrose); Gly (Glycine); Man (Mannitol); Met (L-methionine); Tre (Trehalose).

Materials

D-(−)-Sorbitol (VWR GPR Rectopur™); Polysorbate 80 (Tween80™, Merck™); 140 mg/mL of an anti-FcRn antibody as described in WO2014019727 (SEQ ID NOs: 9 and 10) in 30 mM histidine, 250 mM proline, 0.03% PS80, pH5.6 (UCB Celltech ltd); Mannitol (Roquette™); all the following from (Sigma™): D-(+)-Raffinose pentahydrate, L-Arginine monohydrochloride, L-Histidine, L-Proline, Maltitol, Glycine, Sucrose, L-methionine and Trehalose dehydrate.

Example 1

Freeze-Dried Formulation Preparation

Freeze-drying formulations comprising 100 mg/mL and 80 mg/mL of an anti-FcRn antibody as described in WO2014019727 (SEQ ID NOs: 9 and 10) were prepared by spiking a composition comprising 140 mg/mL of said antibody in 30 mM histidine, pH5.6, 250 mM proline, 0.03% PS80 (reference formulation) with the solutions A-I as indicated in Table 2 below.

TABLE 2

| Ref. | Conc (mg/mL) | Formulation | Conc (mg/mL) | Formulation | |
|---|---|---|---|---|---|
| | | Initial Spiking (100:40) with | | Final | |
| A | N/A | 30 mM histidine pH 5.6, 0.03% PS80, 17.5% sucrose | 100 | 30 mM histidine pH 5.6, 180 mM proline, 0.03% PS80, 5% sucrose | 100-Suc5 |
| B | | 30 mM histidine pH 5.6, 0.03% PS80, 24.5% sucrose | | 30 mM histidine pH 5.6, 180 mM proline, 0.03% PS80, 7% sucrose | 100-Suc7 |
| C | | 30 mM histidine pH 5.6, 0.03% PS80, 14% sorbitol | | 30mM histidine pH 5.6, 180 mM proline, 0.03% PS80, 4% sorbitol | 100-Sor4 |
| D | | 30 mM histidine pH 5.6, 0.03% PS80, 24.5% maltitol | | 30 mM histidine pH 5.6, 180 mM proline, 0.03% PS80, 7% maltitol | 100-Mal7 |
| E | | 30 mM histidine pH 5.6, 0.03% PS80, 35% raffinose | | 30 mM histidine pH 5.6, 180 mM proline, 0.03% PS80, 10% raffinose | 100-Raf10 |
| F | | 30 mM histidine pH 5.6, 0.03% PS80, 630 mM L-arginine | | 30 mM histidine pH 5.6, 180 mM proline, 0.03% PS80, 180 mM L-arginine | 100-Arg180 |
| G | | 30 mM histidine pH 5.6, 0.03% PS80, 250 mM proline | | 30 mM histidine pH 5.6, 250 mM prolineError! Reference source not found., 0.03% PS80 | 100-Pro250 |
| | | Spiking (80:60) with | | Final | |
| H | N/A | 30 mM histidine pH 5.6, 0.03% PS80, 16.5% sucrose | 80 | 30 mM histidine pH 5.6, 180 mM proline, 0.03% PS80, 7% sucrose | 80-Suc7 |
| I | | 30 mM histidine pH 5.6, 0.03% PS80, 21% sucrose | | 30 mM histidine pH 5.6, 180 mM proline, 0.03% PS80, 9% sucrose | 80-Suc9 |

About 3 mL vials (Schott Topline Fiolax™ clear) were filled with 1 mL of freeze-drying formulation. Freeze-drying was done with a Martin-Christ Epsilon 2-6D™ freeze-dryer. A lyophilization cycle consisted of freezing at −40° C., annealing at −10° C., sublimation at −20° C., and secondary drying at 25° C. (Table 3). At the end of the lyophilization cycle vials were filled with approximately 400 mbar N2 and closed with single-vent stoppers (Westar™, West Pharmaceuticals™). Lyophilisates were stored at 2-8° C. until analysis or the start of the stability studies.

TABLE 3

| step | t (h) | ramp (° C./min) | hold (min) | T (° C.) | p (mbar) |
|---|---|---|---|---|---|
| 1 | 0.00 | | 0 | 5 | 1000 |
| 2 | 1.50 | 0.50 | | −40 | 1000 |
| 3 | 2.50 | | 60 | −40 | 1000 |
| 4 | 3.50 | 0.50 | | −10 | 1000 |
| 5 | 5.50 | | 120 | −10 | 1000 |
| 6 | 6.50 | 0.50 | | −40 | 1000 |
| 7 | 8.50 | | 120 | −40 | 1000 |
| 8 | 9.00 | | 30 | −40 | 0.28 |
| 9 | 9.67 | 0.50 | | −20 | 0.28 |
| 10 | 33.67 | | 1440 | −20 | 0.28 |
| 11 | 35.17 | 0.50 | | 25 | 0.28 |
| 12 | 41.17 | | 360 | 25 | 0.28 |
| 13 | 41.50 | 1.00 | | 5 | 0.28 |
| 14 | 50.00 | | 0 | 5 | 0.28 |

The stability studies carried out in these experiments consisted of an accelerated stability study for 3 and 6 months at 30° C., and stressed stability studies for 4 weeks and 3 months at 40° C.).

1. Reconstitution

Lyophilisates were reconstituted with 0.9 mL Milli-Q water to a concentration of 80 or 100 mg/mL respectively. The time for the cake to completely dissolve to a clear solution (with possibly a rim of foam on top) was recorded. Appearance of the lyophilisate and the reconstituted solution was visually assessed.

The reconstitution times are shown in FIG. 1. The reconstitution time is shown on the y-axis in minutes per each of the formulations as per Table 2. The measurements were performed on a formulation reconstituted just after lyophilisation (no storage; t0); after reconstitution of the lyophilised pharmaceutical composition after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.).

Reconstitution times were within 10 minutes for the formulations containing sucrose and for the formulation with 180 mM L-arginine (FIG. 1). Formulation comprising 80 mg/mL of the anti-FcRn antibody reconstituted significantly faster than those formulations comprising 100 mg/mL. Formulations comprising 100 mg/mL of the anti-FcRn antibody in 7% sucrose or in 180 mM L-arginine showed acceptable reconstitution times of less than 10 min at all-time points of the stability studies.

Aggregation

The anti-FcRn antibody concentration was determined by UV absorbance at 280 nm undiluted using a SoloVPE™ (CE Technologies™) extension connected to a Cary50™ UV-visible spectrophotometer (Varian™), or after dilution in water to 1 mg/mL with a Spectramax™ M5 plate reader (Molecular Devices™), $\varepsilon=1.34$ mL·mg$^{-1}$·cm$^{-1}$.

The quantity of protein aggregation was determined by size-exclusion UPLC (SE-UPLC) using two Acquity™ BEH200 SEC (Waters) 1.7 μm, 4.6×150 mm columns in series and 0.1M Na-phosphate, 0.3M NaCl, pH7.0 running buffer (0.3 mL/min). Detection and quantitation were performed by fluorescence (ex 280 nm, em 345 nm).

Protein aggregation was also evaluated by dynamic light scattering (DLS) using a DynaPro Plate Reader™ (Wyatt™). Sample aliquots diluted to 10 mg/mL in 30 mM histidine pH 5.6 were measured (10 acquisitions of 5 sec). Data were analyzed with the Dynamics™ 7.1.4 regularization fit for multimodal particle distribution (Wyatt™).

Figure 2:
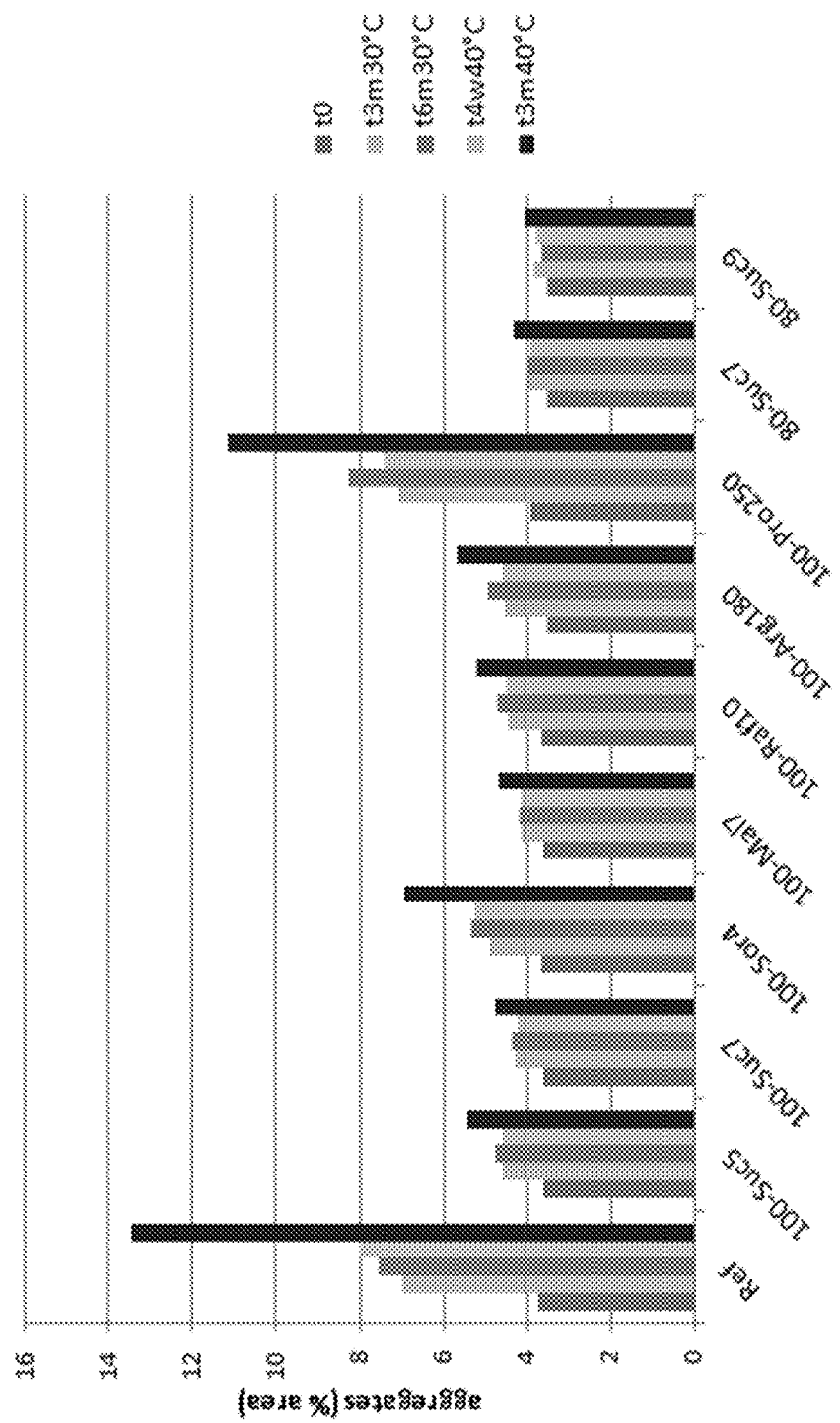
FIG. 2. Aggregates formation by SEC. Total aggregates as % area are shown on the y-axis per each of the formulations (x-axis) of Table 2.

Data are shown in FIG. 2 as the total percentage of aggregates determined by SE UPLC per each formulation. The reference formulation (140 mg/mL of the anti-FcRn antibody in 30 mM histidine, pH5.6, 250 mM proline, 0.03% PS80; not lyophilised) was also investigated (Ref in FIG. 2). Measurements were performed on a formulation reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.).

Except for the proline formulation (100-Pro250) all formulations showed an increased stability towards aggregation compared to the reference formulation (FIG. 2). In particular formulations containing ≥7% sucrose showed good stability towards aggregation both as absolute aggregate formation per each stability study and as a rate of aggregate formation over studies conducted at 30° C. and 40° C. A formulation comprising 100 mg/mL of the anti-FcRn antibody in 30 mM histidine pH5.6, 180 mM proline, 7% sucrose, 0.03% PS80 showed an increase in aggregates of only 0.2%/month at 30° C. and 0.4%/month at 40° C. (Table 4).

TABLE 4

| | aggr (% area) | | | | | aggr rate (% area/month) | |
|---|---|---|---|---|---|---|---|
| | $t_0$ | $t_{3\,m\,30°\,C.}$ | $t_{6\,m\,30°\,C.}$ | $t_{4\,w\,40°\,C.}$ | $t_{3\,m\,40°\,C.}$ | 30° C. | 40° C. |
| Ref | 3.7 | 7.0 | 7.6 | 8.0 | 13.5 | 0.9 | 3.8 |
| 100-Suc5 | 3.6 | 4.6 | 4.8 | 4.6 | 5.4 | 0.3 | 0.8 |
| 100-Suc7 | 3.6 | 4.3 | 4.4 | 4.2 | 4.8 | 0.2 | 0.5 |
| 100-Sor4 | 3.6 | 4.9 | 5.4 | 5.3 | 6.9 | 0.4 | 1.4 |
| 100-Mal7 | 3.6 | 4.2 | 4.2 | 4.1 | 4.7 | 0.1 | 0.5 |
| 100-Raf10 | 3.6 | 4.5 | 4.7 | 4.5 | 5.2 | 0.2 | 0.7 |
| 100-Arg180 | 3.5 | 4.6 | 4.9 | 4.6 | 5.6 | 0.3 | 0.9 |
| 100-Pro250 | 3.9 | 7.1 | 8.3 | 7.4 | 11.1 | 1.0 | 3.1 |
| 80-Suc7 | 3.5 | 4.0 | 4.0 | 3.9 | 4.3 | 0.1 | 0.3 |
| 80-Suc9 | 3.5 | 3.8 | 3.7 | 3.8 | 4.1 | 0.1 | 0.2 |

Maltitol showed also acceptable aggregate formation, in line with what observed with ≥7% sucrose. Whilst arginine and maltitol showed reasonable results in the reconstitution time and aggregate formation, respectively, they did not provide acceptable results in both tests, unlike ≥7% sucrose which provided low reconstitution time, low aggregate formation and rate of formation.

Aggregates not detected by SE UPLC were investigated by DLS. The percentage aggregates determined by DSL using the percentage intensity size distribution is shown per each of the lyophilised compositions, before lyophilisation and on formulations reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.).

Figure 3:
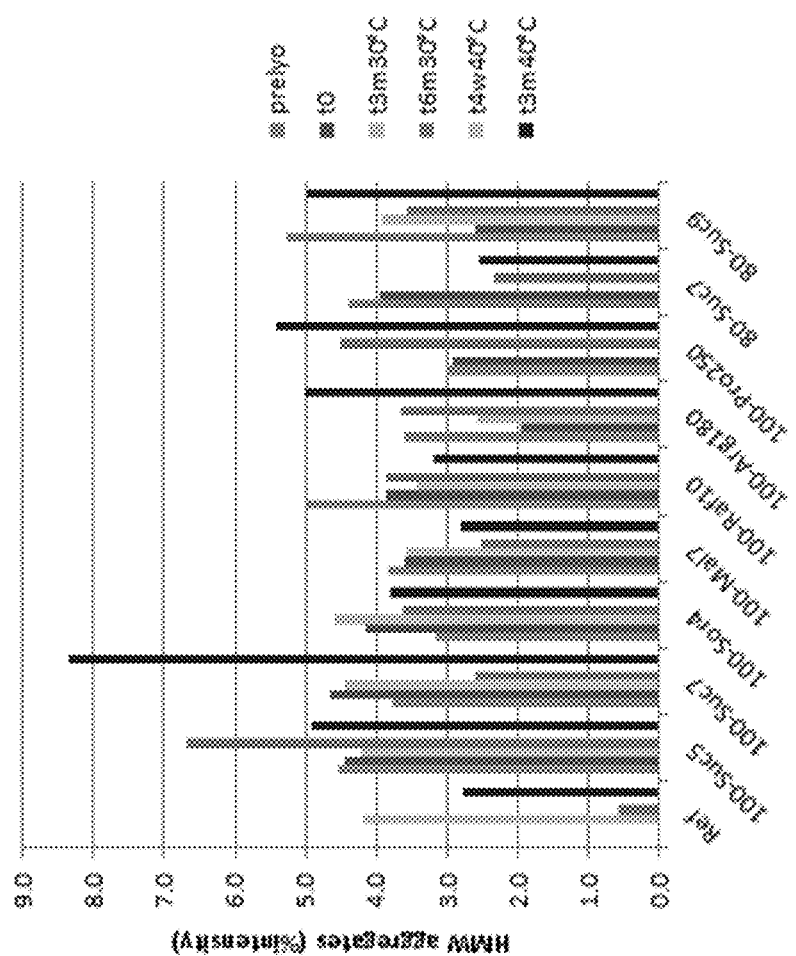
FIG. 3. HMW aggregate formation by DLS. Intensities (as %) were plotted on the y-axis per each formulation (x-axis) of Table 2.

The reference formulation (140 mg/mL of the anti-FcRn antibody in 30 mM histidine, pH5.6, 250 mM proline, 0.03% PS80; not lyophilised) was also investigated. Neither the reference (Ref) nor the freeze-dried formulations showed a significant amount of HMW aggregates. No significant change in large or HMW aggregates upon stability was observed by DLS (FIG. 3) as the measured variations in intensity are not significant and inherent to the measurement technique.

Charge Variants

Charge variants were determined by imaged capillary electrophoresis (iCE with iCE3 (Protein Simple™). Measurements were performed on formulations reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.).

Figure 4:
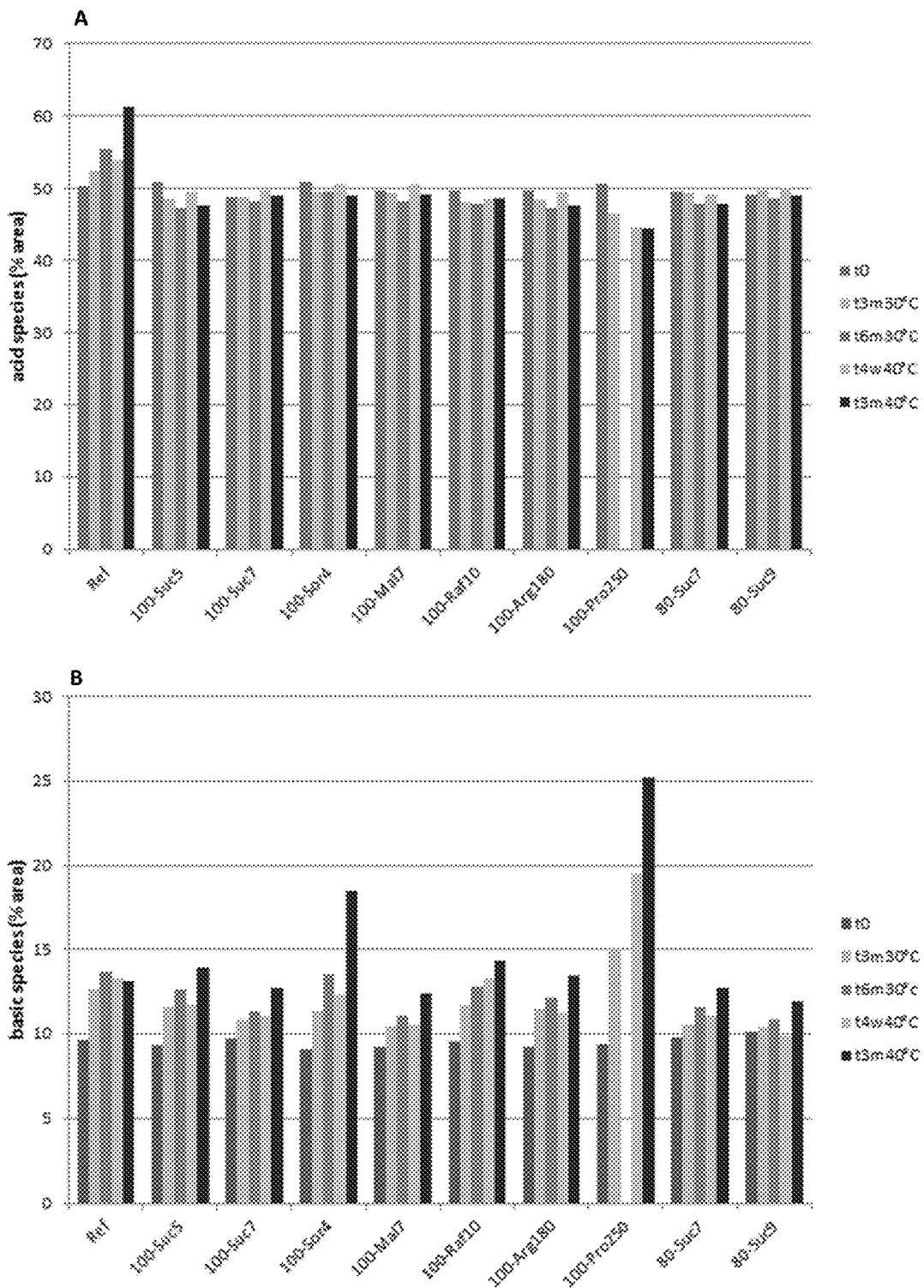
FIG. 4. Charge variants. The formation of acidic (A) and basic (B) variants was plotted as a function of the % area (y-axis) per each formulation (x-axis) of Table 2.

An increase in acidic species (FIG. 4A) was observed for the reference formulation (140 mg/mL of the anti-FcRn antibody in 30 mM histidine, pH5.6, 250 mM proline, 0.03% PS80; not lyophilised). The formulation containing 250 mM proline showed a decrease in acidic species but it also showed a significant increase in basic species (FIG. 4B). The formulation comprising 4% sorbitol also showed a marked increase in basic species. The remaining freeze-dying formulations did show only a minor increase in basic species and no significant change in acidic species (FIG. 4A ad 4B). The formulations comprising ≥7% sucrose did not show any significant charge variants changes.

Viscosity

Viscosity of reconstituted product was measured with a ViscoPro2000™ viscometer (Cambridge Viscosity). Measurements were performed on formulations reconstituted just after lyophilisation (no storage) at 22+/−1° C.

Figure 5:
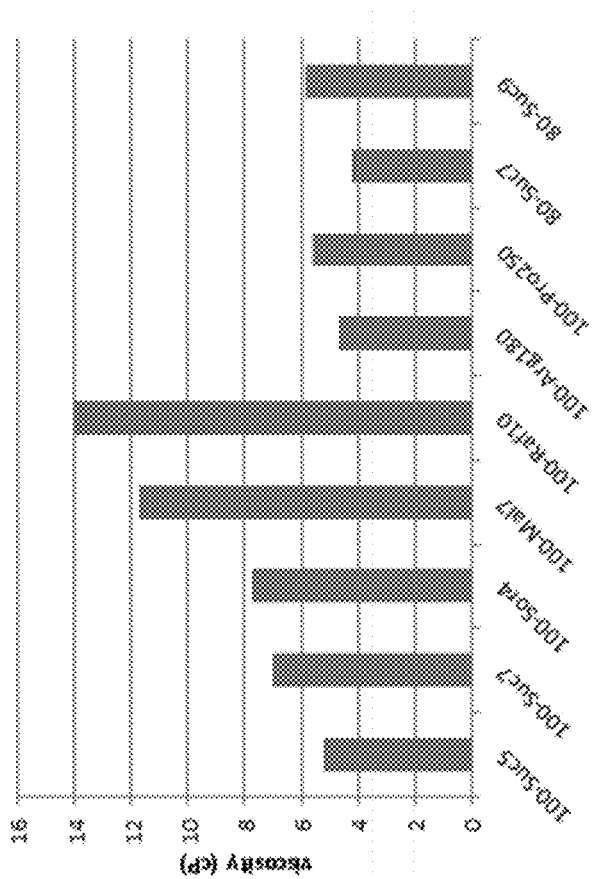
FIG. 5. Viscosity. The viscosity (cP) is shown on the y-axis per each formulation (x-axis) of Table 2.

Viscosity increased with increasing sugar/sugar alcohol concentration or with increasing sugar/sugar alcohol molecular weight (FIG. 5). The viscosity for the formulation comprising 80 and 100 mg/mL in sucrose freeze-drying formulation were all acceptable. The formulation comprising 100 mg/mL of the anti-FcRn antibody in combination with 180 mM L-arginine showed also acceptable viscosity. Arginine is a recognised excipient which is commonly added to pharmaceutical compositions to reduce the viscosity. Its effect was comparable to the formulation comprising sucrose.

Osmolality

Osmolality of reconstituted formulations was measured with a Vapro™ 5520 vapor pressure osmometer (Wescor™). Measurements were performed on formulations reconstituted just after lyophilisation (no storage).

Figure 6:
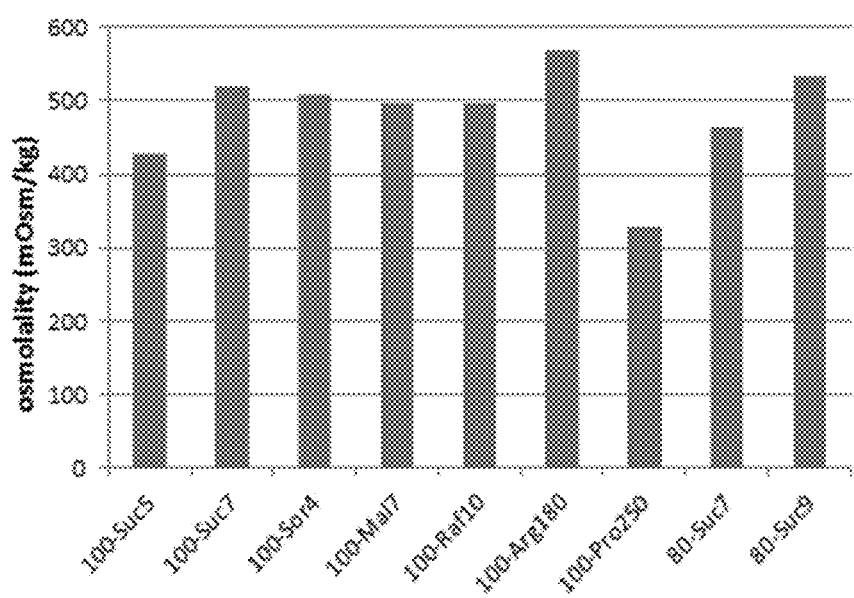
FIG. 6. Osmolality. The Osmolality (mOsm/kg) is shown on the y-axis per each formulation (x-axis) of Table 2.

Most formulations showed an osmolality of around 500 mOsm/kg (FIG. 6). The formulation comprising 100 mg/mL of the anti-FcRn antibody in the 180 mM L-arginine formulation showed the highest osmolality (570 mOsm/kg), whilst formulation comprising 100 mg/mL of the anti-FcRn antibody in the 250 mM proline formulation showed the lowest osmolality (330 mOsm/kg). The formulation comprising sucrose showed acceptable osmolality.

Example 2

Freeze-drying formulations (Table 5), except for the reference formulation, were prepared from 60 mg/mL the anti-FcRn antibody in 30 mM histidine, 250 mM sorbitol, pH5.6 by buffer exchange using Amicon™ Ultra-15 30K (Millipore™) centrifugal filter/concentration devices for volumes up to 15 mL with at least 4 cycles of dilution/concentration using in total a diavolume of at least 7 times the volume of the original sample to the final compositions according to Table 5 at pH5.6. Polysorbate 20 (PS20) was added after buffer exchange from a filtered 3% PS20 stock solution to a final concentration of 0.03%. Formulation B of Example 1 (100 mg/ml of the anti-FcRn antibody, 7% sucrose, 30 mM histidine, 180 mM proline and 0.03% PS80, pH 5.6) was chosen as the reference formulation for the experiments of Example 2.

Vials (3 mL; Topline Fiolac clear, Schott™) were filled with 1 mL of formulation comprising 100 mg/mL or 140 mg/mL of the anti-FcRn antibody (indicated by * are formulations tested at both concentrations of 100 mg/ml and 140 mg/ml) (Table 5). Freeze-drying was performed as for Example 1.

TABLE 5

| Formulation | | % w/v | mM | | % w/v | mM | | % w/v | | mM |
|---|---|---|---|---|---|---|---|---|---|---|
| Reference | Sucrose | 7 | 204 | L-proline | | 180 | PS80 | 0.03 | histidine | 30 |
| Suc7 | | 7 | 204 | | N/A | N/A | PS20 | 0.03 | histidine | 30 |
| Suc10* | | 10 | 292 | | N/A | N/A | | | | |
| Suc13 | | 13 | 380 | | N/A | N/A | | | | |
| Suc5Man4 | | 5 | 146 | Mannitol | 4 | 220 | | | | |
| Suc6Man3* | | 6 | 175 | | 3 | 165 | | | | |
| Suc7Man2 | | 7 | 204 | | 2 | 110 | | | | |
| Suc5Arg4 | | 5 | 146 | L-arginineHCl | 4 | 190 | | | | |
| Suc6Arg3* | | 6 | 175 | | 3 | 142 | | | | |
| Suc7Arg2 | | 7 | 204 | | 2 | 95 | | | | |
| Suc5Gly2 | | 5 | 146 | Glycine | 2 | 266 | | | | |
| Suc6Gly1.5* | | 6 | 175 | | 1.5 | 200 | | | | |
| Suc7Gly1 | | 7 | 204 | | 1 | 133 | | | | |
| Suc5Met3 | | 5 | 146 | L- | 3 | 201 | | | | |

TABLE 5-continued

| Formulation | | % w/v | mM | | % w/v | mM | % w/v | mM |
|---|---|---|---|---|---|---|---|---|
| Suc6Met2.25* | | 6 | 175 | methionine | 2.25 | 151 | | |
| Suc7Met1.5 | | 7 | 204 | | 1.5 | 100 | | |
| Tre10* | Trehalose (dihydrate) | 10 | 264 | | N/A | N/A | | |

Reconstitution

Figure 7:
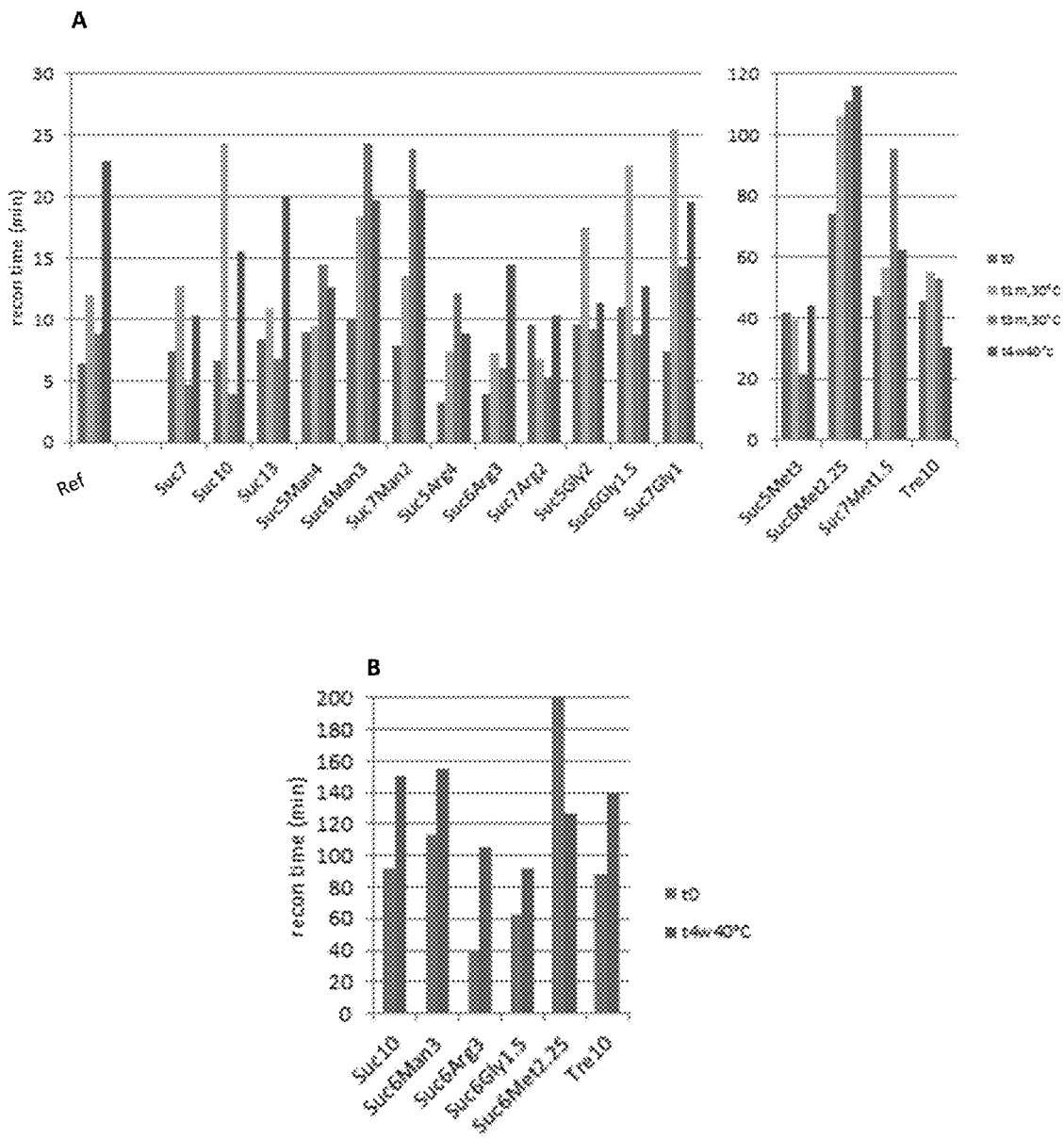
FIG. 7. Reconstitution time upon lyophilisation. Reconstitution time (recon time) is shown on the y-axis in minutes per each of the formulations (x-axis) of Table 5.

Reconstitution was carried out as per Example 1. Measurements were performed on formulations reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.). Relatively rapid reconstitution was achieved for sucrose, sucrose-glycine and sucrose-arginine formulations, both at 100 mg/mL and 140 mg/mL of the anti-FcRn antibody (FIG. 7A, FIG. 7B). Sucrose-mannitol formulations did not reconstitute comparably fast, whilst methionine formulations and the trehalose formulation required long time to reconstitute (see different y-axis scale in FIG. 7A). The difference between the 10% sucrose and the 10% trehalose formulation is surprising and suggests a specific interaction between sucrose and the anti-FcRn antibody aiding reconstitution. The negative influence of methionine on reconstitution could be due to change in the structure of the lyophilized cake, but also to molecular changes of the anti-FcRn antibody (more evident in the aggregation analysis below).

Aggregation

Figure 8:
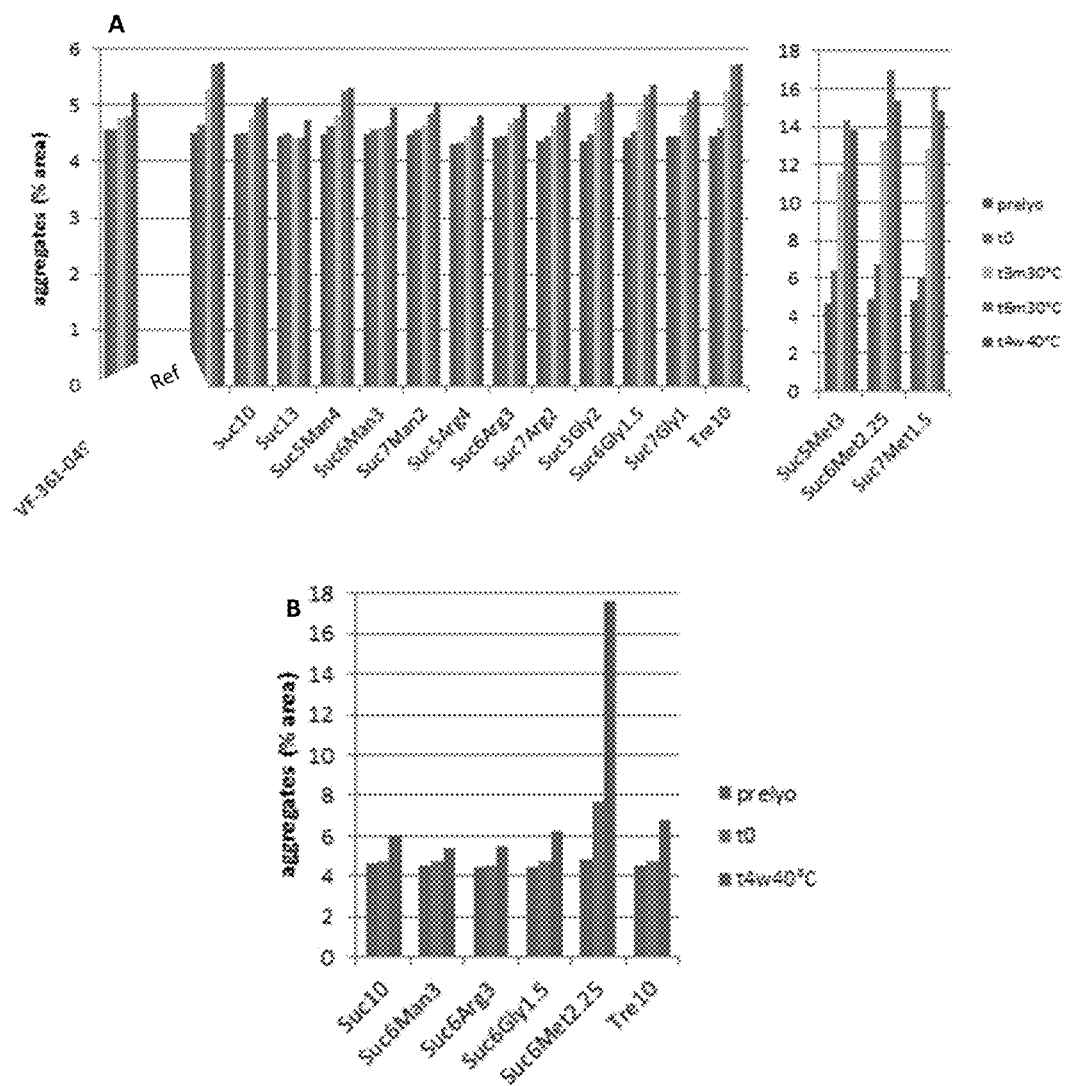
FIG. 8. Aggregates formation by SEC. Total aggregates as % area are shown on the y-axis per each of the formulations (x-axis) of Table 5.

Aggregation was investigated according to the method of Example 1. Measurements were performed on formulations prior lyophilisation, on formulations reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.). All formulations, except for the methionine containing formulation, at both concentrations (100 mg/ml and 140 mg/mL) of the anti-FcRn antibody, showed good stability towards aggregation (FIGS. 8A and 8B). Formulations showing the highest stability towards aggregation included the 10% and 13% sucrose formulations, the 6% sucrose-3% mannitol and 7% sucrose-2% mannitol formulations, all arginine containing formulations, and the reference formulation (containing 7% sucrose and proline). Aggregation levels for formulation containing 140 mg/mL of the anti-FcRn antibody were similar to those containing 100 mg/mL. Methionine-containing formulations showed a high degree of aggregate formation at both concentrations of the anti-FcRn antibody.

Figure 9:
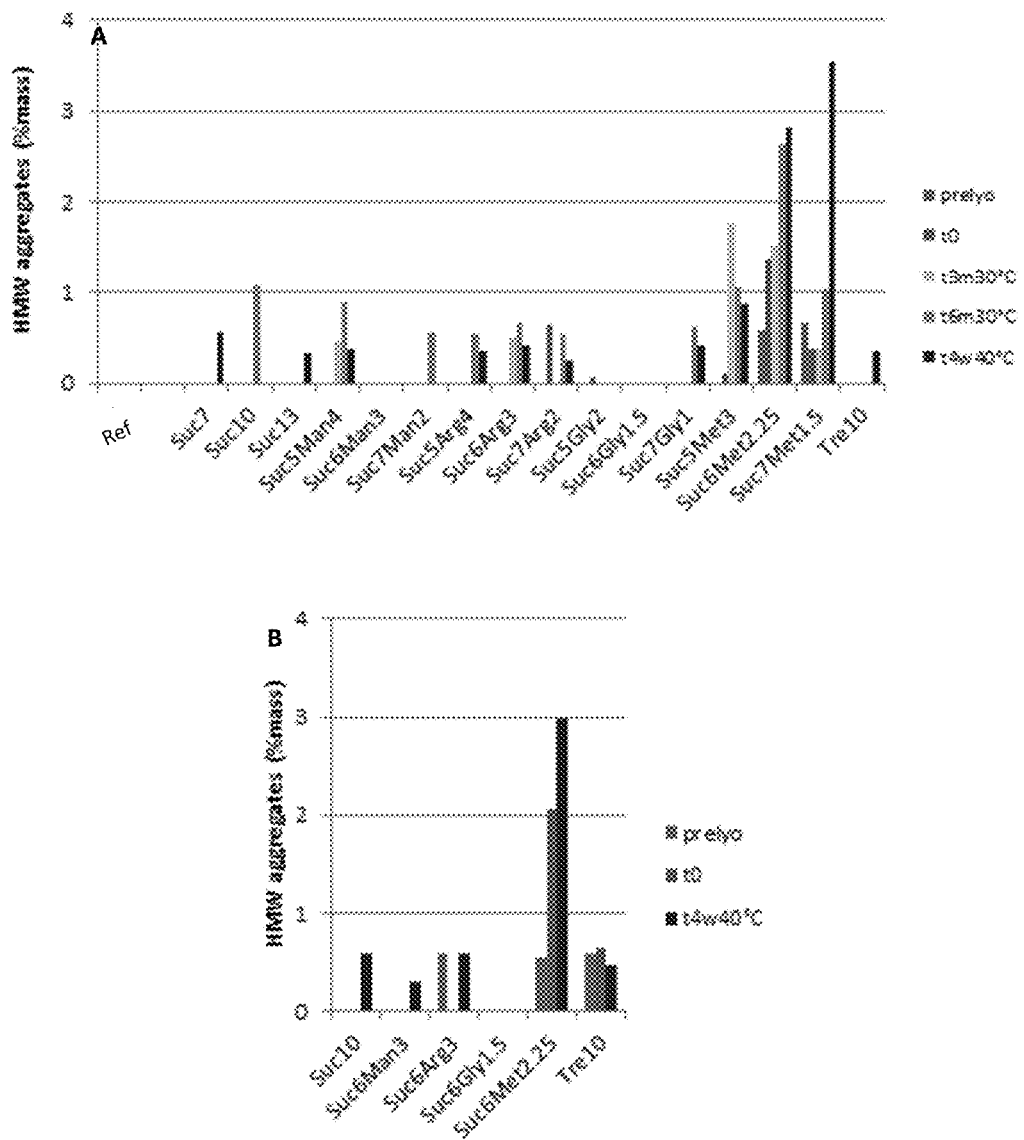
FIG. 9. HMW aggregate formation by DLS. Masses (as %) were plotted on the y-axis per each formulation (x-axis) of Table 5.

High molecular weight (HMVV) aggregates were also investigated. The percentage aggregates determined by DSL using the percentage mass size distribution was shown per each of the lyophilised formulations, before lyophilisation and on formulations reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.). Results are shown in FIGS. 9A and 9B. Except for methionine-containing formulations, no significant increase in high molecular weight (HMVV) aggregates, as measured by DLS, was observed. The increase in HMW aggregates for methionine formulations correlates well with the SE-UPLC data. Aggregation appears to be induced by thermal stress and not by freeze-drying.

Charge Variants

Figure 10:
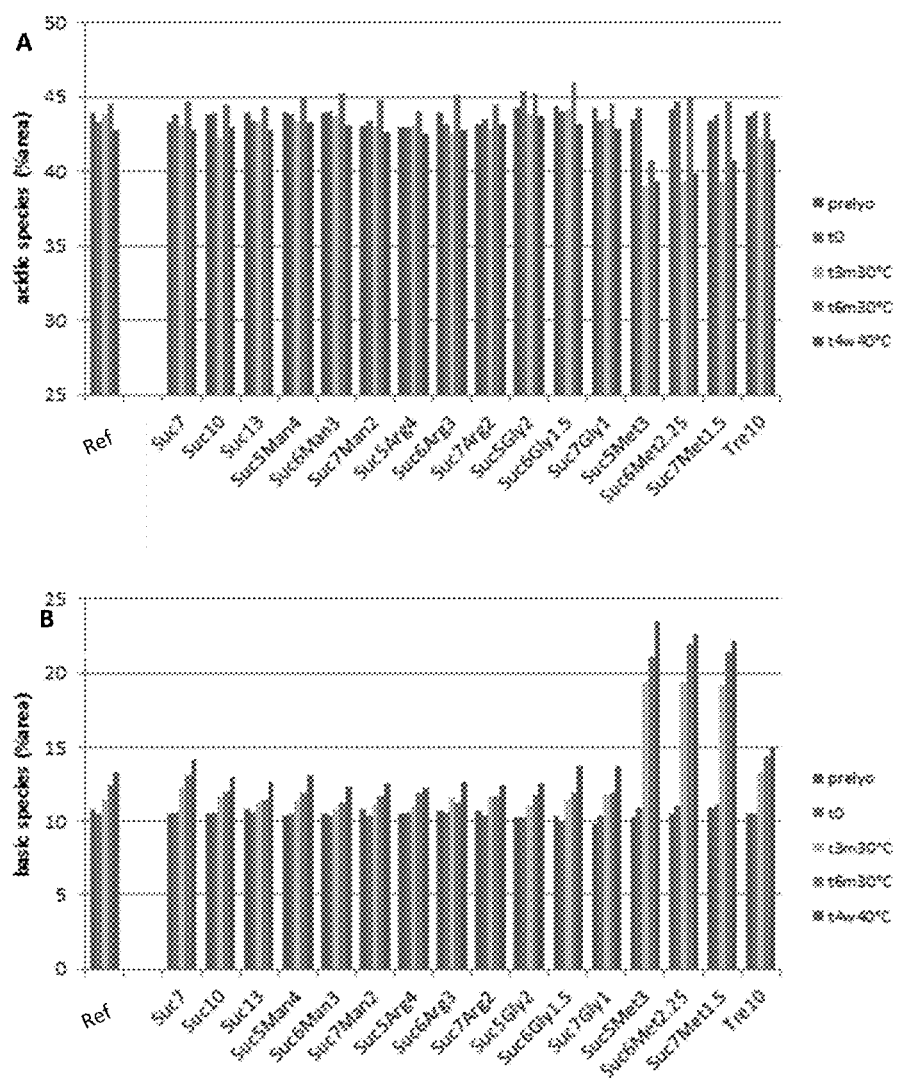
FIG. 10. Charge variants. The formation of acidic (A) and basic (B) variants was plotted as a function of the % area (y-axis) per each formulation (x-axis) of Table 5 comprising the anti-FcRn antibody at 100 mg/mL.
Figure 11:
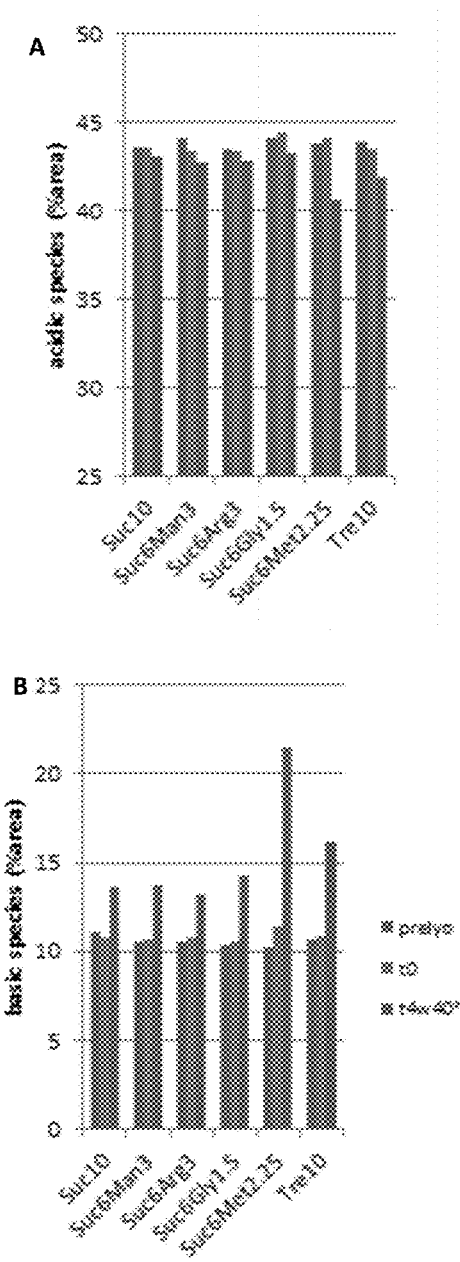
FIG. 11. Charge variants. The formation of acidic (A) and basic (B) variants was plotted as a function of the % area (y-axis) per each formulation (x-axis) of Table 5 comprising an anti-FcRn antibody at 140 mg/mL.

Charge variant analysis was carried out as per Example 1. Measurements were performed on pharmaceutical compositions prior lyophilisation, on formulations reconstituted just after lyophilisation (no storage; t0); after reconstitution of the lyophilised pharmaceutical compositions after storage for 3 months at 30° C. (t3m, 30° C.); after 6 months at 30° C. (t6m, 30° C.); after 4 weeks at 40° C. (t4w, 40° C.) and after 3 months at 40° C. (t3m, 40° C.). For the formulations comprising 100 mg/mL of the anti-FcRn antibody, a decrease in acidic species and an increase in basic species were observed for the methionine formulations after storage at 30° C. and 40° C. (FIGS. 10A and 10B). A similar behaviour was confirmed for the formulations comprising 140 mg/mL of the anti-FcRn antibody and methionine (FIGS. 11A and 11B). This suggests thermally induced chemical changes in the anti-FcRn antibody due to the presence of methionine, which may also be the reason for the aggregation behavior of the anti-FcRn antibody. For all other formulations no significant changes in charge variants were observed.

Viscosity

Figure 12:
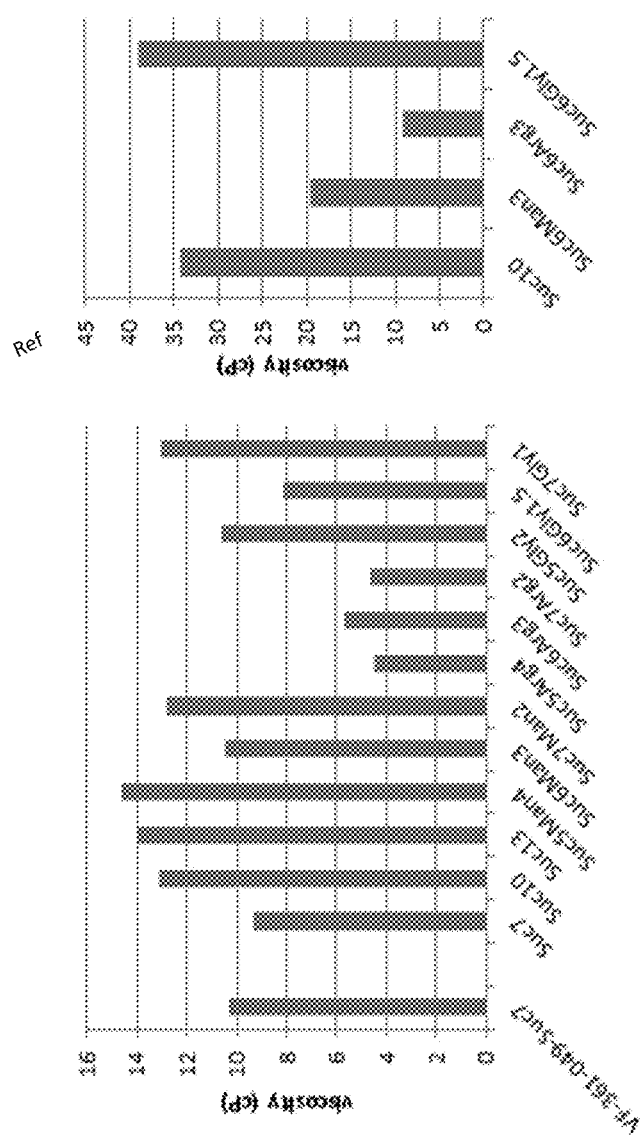
FIG. 12. Viscosity. The viscosity (cP) is shown on the y-axis per each formulation (x-axis) of Table 5.
Figure 13:
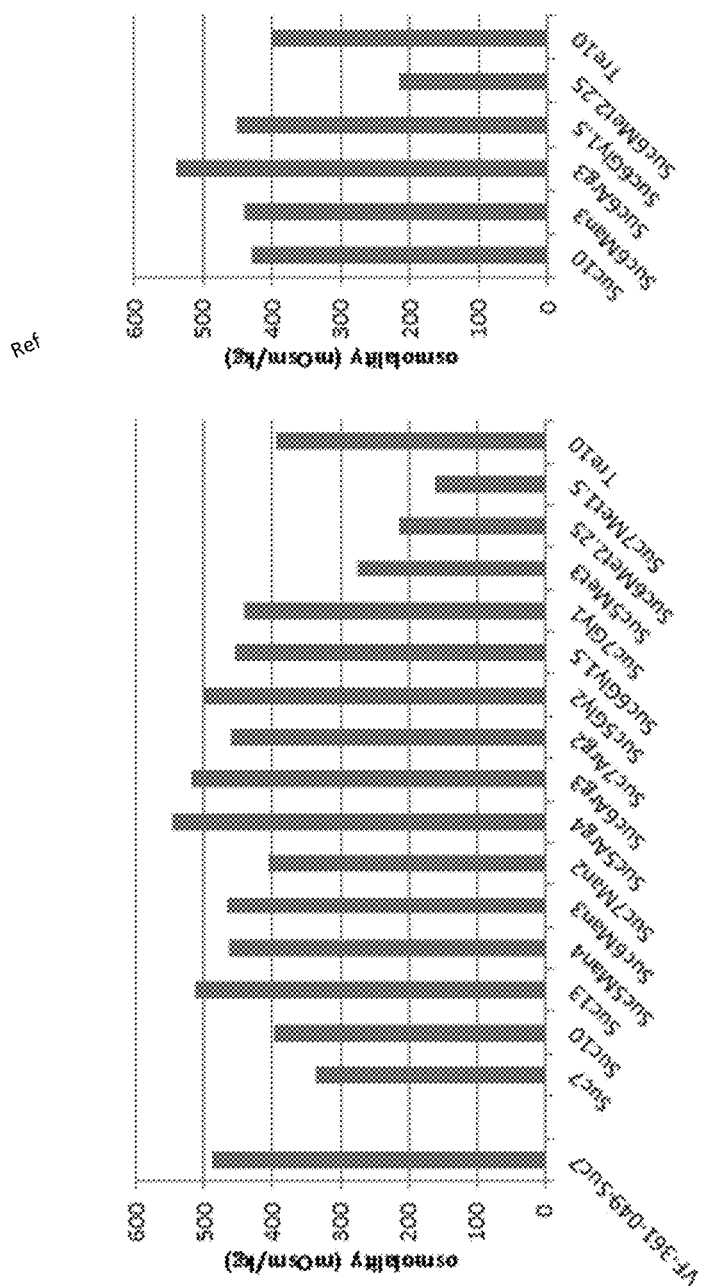
FIG. 13. Osmolality. The Osmolality (mOsm/kg) is shown on the y-axis per each formulation (x-axis) of Table 5.

Viscosity of reconstituted product was measured with a ViscoPro2000™ viscometer (Cambridge Viscosity™). Measurements were performed on formulation reconstituted just after lyophilisation (no storage). Viscosity was very low (<6 cP) for arginine containing formulations, even at 140 mg/mL (FIG. 12). For all other formulations, the viscosity was higher than >8 cP.

Osmolality

Osmolality of reconstituted formulations was measured with a Vapro™ 5520 vapor pressure osmometer (Wescor™). Measurements were performed on formulation reconstituted just after lyophilasition (no storage). All formulations with good stability and reconstitution characteristics, such as the formulations comprising 7% sucrose showed acceptable osmolality. Remarkably, methionine-containing formulations showed a very low osmolality.

The invention claimed is:

1. A pharmaceutical composition comprising:
   a. an antibody or an antigen-binding fragment thereof comprising a light variable region as defined in SEQ ID NO: 7 and a heavy variable region as defined in SEQ ID NO: 8 and having a concentration of from 80 to 200 mg/mL;
   b. from 7% to 13% w/v sucrose;
   c. a mixture of 10 mM to 50 mM histidine and 180 mM proline;
   d. 0.01% to 1.0% surfactant; and
   e. a pH of from 4.0 to 7.5.

2. The pharmaceutical composition according to claim 1, wherein the antibody or antigen-binding fragment thereof is at a concentration of from 80 to 140 mg/mL.

3. The pharmaceutical composition according to claim 1, wherein the composition comprises from 7% to 10% w/v sucrose.

4. The pharmaceutical composition according to claim 1, wherein the composition comprises 0.01 to 0.5% w/v of the surfactant.

5. The pharmaceutical composition according to claim 4, wherein the surfactant is polysorbate 80.

6. The pharmaceutical composition according to claim 1, wherein the antibody is a human or humanised antibody.

7. The pharmaceutical composition according to claim 1, wherein the composition comprises from 80 mg/mL to 140 mg/mL of antibody or antigen-binding fragment thereof, 30 mM histidine, from 180 mM proline, 7% w/v sucrose, 0.03% w/v polysorbate 80, at pH 5.6.

8. The pharmaceutical composition according to claim 1, wherein the composition further comprises mannitol and/or arginine and/or glycine.

9. A freeze-dried formulation comprising an antibody or an antigen-binding fragment thereof, sucrose, an amino acid or a mixture of histidine and proline, and optionally a surfactant, wherein the formulation comprises from 20% to 40% w/w sucrose, wherein the antibody or antigen-binding fragment thereof comprises a light variable region as defined in SEQ ID NO: 7 and a heavy variable region as defined in SEQ ID NO: 8 and wherein the antibody or antigen-binding fragment thereof had, before freeze-drying, a concentration of 80 to 200 mg/mL, 10 mM to 50 mM of the histidine, 180 mM of the proline; and if present 0.01% to 1.0% w/v of the surfactant.

10. A liquid pharmaceutical formulation comprising the freeze-dried formulation of claim 9 and a solvent.

11. A container comprising the freeze-dried formulation of claim 9 or a liquid pharmaceutical formulation comprising the freeze-dried formulation.

12. The freeze-dried formulation according to claim 9, wherein said formulation comprises about 50.8% w/w of the antibody or antigen-binding fragment thereof, about 35.5% w/w sucrose, about 3.0% w/w histidine, about 10.5% w/w proline and 0.2% w/w polysorbate 80.

* * * * *

SEQUENCE LISTING

<160> NUMBER OF SEQ ID NOS: 11

<210> SEQ ID NO 1
<211> LENGTH: 10

```
<212> TYPE: PRT
<213> ORGANISM: Artificial Sequence
<220> FEATURE:
<223> OTHER INFORMATION: CDR-H1

<400> SEQUENCE: 1

Gly Phe Thr Phe Ser Asn Tyr Gly Met Val
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR-H2

<400> SEQUENCE: 2

Tyr Ile Asp Ser Asp Gly Asp Asn Thr Tyr Tyr Arg Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: CDR-H3

<400> SEQUENCE: 3

Gly Ile Val Arg Pro Phe Leu Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: CDR-L1

<400> SEQUENCE: 4

Lys Ser Ser Gln Ser Leu Val Gly Ala Ser Gly Lys Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

Leu Val Ser Thr Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR-L3

<400> SEQUENCE: 6

Leu Gln Gly Thr His Phe Pro His Thr
1               5

<210> SEQ ID NO 7
```

<211> LENGTH: 112
<212> TYPE: PRT
<213> ORGANISM: Artificial Sequence
<220> FEATURE:
<223> OTHER INFORMATION: Light Chain Variable Region

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

<210> SEQ ID NO 8
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 8

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser
        115

<210> SEQ ID NO 9
<211> LENGTH: 219
<212> TYPE: PRT
<213> ORGANISM: Artificial Sequence
<220> FEATURE:
<223> OTHER INFORMATION: Ligh Chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

```
Ser Gly Lys Thr Tyr Leu Tyr Trp Leu Phe Gln Lys Pro Gly Lys Ala
         35                  40                  45

Pro Lys Arg Leu Ile Tyr Leu Val Ser Thr Leu Asp Ser Gly Ile Pro
 50                  55                  60

Ser Arg Phe Ser Gly Ser Gly Ser Gly Thr Glu Phe Thr Leu Thr Ile
 65                  70                  75                  80

Ser Ser Leu Gln Pro Glu Asp Phe Ala Thr Tyr Tyr Cys Leu Gln Gly
                 85                  90                  95

Thr His Phe Pro His Thr Phe Gly Gln Gly Thr Lys Leu Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 444
<212> TYPE: PRT
<213> ORGANISM: Artificial Sequence
<220> FEATURE:
<223> OTHER INFORMATION: Heavy chain

<400> SEQUENCE: 10

Glu Val Pro Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Asn Tyr
             20                  25                  30

Gly Met Val Trp Val Arg Gln Ala Pro Gly Lys Gly Leu Glu Trp Val
         35                  40                  45

Ala Tyr Ile Asp Ser Asp Gly Asp Asn Thr Tyr Tyr Arg Asp Ser Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Val Tyr Tyr Cys
                 85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 11
<211> LENGTH: 220
<212> TYPE: PRT
<213> ORGANISM: Artificial Sequence
<220> FEATURE:
<223> OTHER INFORMATION: Fab heavy chain

<400> SEQUENCE: 11

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

```
                        -continued
Thr Thr Gly Ile Val Arg Pro Phe Leu Tyr Trp Gly Gln Gly Thr Leu
            100                 105             110

Val Thr Val Ser Ser Ala Ser Thr Lys Gly Pro Ser Val Phe Pro Leu
        115                 120             125

Ala Pro Ser Ser Lys Ser Thr Ser Gly Gly Thr Ala Ala Leu Gly Cys
        130                 135             140

Leu Val Lys Asp Tyr Phe Pro Glu Pro Val Thr Val Ser Trp Asn Ser
145                 150                 155             160

Gly Ala Leu Thr Ser Gly Val His Thr Phe Pro Ala Val Leu Gln Ser
                165                 170             175

Ser Gly Leu Tyr Ser Leu Ser Ser Val Val Thr Val Pro Ser Ser Ser
            180                 185             190

Leu Gly Thr Gln Thr Tyr Ile Cys Asn Val Asn His Lys Pro Ser Asn
            195                 200             205

Thr Lys Val Asp Lys Lys Val Glu Pro Lys Ser Cys
210                 215                 220
```